US012669496B2

(12) United States Patent
Kimura et al.

(10) Patent No.: US 12,669,496 B2
(45) Date of Patent: Jun. 30, 2026

(54) METHOD FOR EVALUATING AND/OR SCREENING A CONTROL AGENT FOR TISSUE MORPHOLOGY AND/OR TISSUE FUNCTION

(71) Applicants: ROHTO PHARMACEUTICAL CO., LTD., Osaka (JP); RIKEN, Wako (JP)

(72) Inventors: Shun Kimura, Osaka (JP); Takashi Tsuji, Wako (JP)

(73) Assignees: ROHTO PHARMACEUTICAL CO., LTD., Osaka (JP); RIKEN, Wako (JP)

( * ) Notice: Subject to any disclaimer, the term of this patent is extended or adjusted under 35 U.S.C. 154(b) by 917 days.

(21) Appl. No.: 17/793,184

(22) PCT Filed: Oct. 19, 2020

(86) PCT No.: PCT/JP2020/039220
§ 371 (c)(1),
(2) Date: Jul. 15, 2022

(87) PCT Pub. No.: WO2021/145038
PCT Pub. Date: Jul. 22, 2021

(65) Prior Publication Data
US 2023/0057222 A1    Feb. 23, 2023

Related U.S. Application Data

(60) Provisional application No. 62/962,267, filed on Jan. 17, 2020.

(51) Int. Cl.
*G01N 33/50* (2006.01)
(52) U.S. Cl.
CPC ................................. *G01N 33/5008* (2013.01)
(58) Field of Classification Search
None
See application file for complete search history.

(56) References Cited

U.S. PATENT DOCUMENTS

2003/0064358 A1 *    4/2003    Elson .................. G01N 33/5061
                                                                    435/325
2004/0142335 A1 *    7/2004    Petersohn .......... G01N 33/6881
                                                                    435/6.1
2017/0304167 A1    10/2017    Tate et al.

FOREIGN PATENT DOCUMENTS

JP        2006-131570 A    5/2006
JP        2014-41043 A    3/2014
JP        2019-199441 A    11/2019
WO    WO 2016/063847 A1    4/2016

OTHER PUBLICATIONS

International Search Report (PCT/ISA/210) issued in PCT/JP2020/039220 mailed on Dec. 8, 2020.
Kimura et al., "Analysis of skin remodeling mechanism by tensile loading in artificial skin model", Programs and abstracts of the 18th congress of the Japanese society for regenerative medicine, Feb. 22, 2019, pp. 499, O-22-5, entire text, non-official translation.
Miyasaka et al., "Mechanical stress and transcriptional control", The Journal of Biochemistry, 2009, vol. 81, No. 6, pp. 494-501, Total 9 pages.
Takada et al., "Analysis of the role of mechanical stress and mechanosignaling in skin epidermal cells", Fragrance Journal, Mar. 15, 2012, vol. 40, No. 3, pp. 65-69, entire text, all drawings, non-official translation.
Written Opinion (PCT/ISA/237) issued in PCT/JP2020/039220 mailed on Dec. 8, 2020.
Yagi et al., "Stress Response and Cardiac Pathophysiology Mechanical Stress Response", Department of Cardiovascular Medicine, Graduate School of Medicine, The University of Tokyo, HEART's Selection 1, 2015, vol. 47, No. 12, pp. 1372-1378. Total 9 pages.
Yamashiro et al., "Matrix mechanotransduction mediated by thrombospondin-1/integrin/YAP in the vascular remodeling", PNAS, May 5, 2020, vol. 117, No. 18, pp. 9896-9905.

* cited by examiner

*Primary Examiner* — Nghi V Nguyen
(74) *Attorney, Agent, or Firm* — Birch, Stewart, Kolasch & Birch, LLP

(57) ABSTRACT

An object of the present invention is to provide a new method for evaluating and/or screening an excellent healthcare material or pharmaceutical product based on a new concept. The present invention to solve the above object is a method for evaluating and/or screening a control agent for tissue morphology and/or tissue function, the method including: applying a test substance to a tissue or cell capable of expressing a mechanical stress signaling molecule; and evaluating expression, activity, or intracellular localization of the mechanical stress signaling molecule in the tissue or cell.

13 Claims, 19 Drawing Sheets

COL1

Bell-shaped

Tensional-homeostatic

Tension-released

Ki67

Bell-shaped

Tensional-
homeostatic

Tension-
released

Control　　　　　　　　　　　　ATRA

Merge

Type I
collagen

Integrin β1

FIG. 14

COL1

Tensional-
homeostatic

Tensional-
homeostatic
+ Y27632

Tension-
released

METHOD FOR EVALUATING AND/OR SCREENING A CONTROL AGENT FOR TISSUE MORPHOLOGY AND/OR TISSUE FUNCTION

TECHNICAL FIELD

The present invention relates to a method for evaluating and/or screening a control agent for tissue morphology and/or tissue function.

BACKGROUND ART

Decline or change in functions of cells constituting tissues has been pointed out as a cause of various diseases and aging. As pharmacological approaches to ameliorate these, drug discovery materials, such as small molecule compounds, nucleic acids, and proteins, are investigated. However, such approaches may often fail to exert adequate therapeutic/amelioration effect depending on the type and symptom of disease or the like, and a solution based on a new concept is required.

On the other hand, studies in recent years have revealed that mechanical stress controls the functionality of tissues or cells and is involved in aging and onset of conditions, and in the fields where adequate therapeutic/amelioration methods have not been developed so far, the possibility of healthcare material development and drug discovery focusing on mechanical stress has been investigated. For example, the importance of mechanical stress response in the pathophysiology of heart failure and therapeutic strategies based on it have been also investigated (see Non-Patent Literature 1). In addition, in the field of drug discovery, a molecule that, when administered orally, exerts an effect equivalent to movement, using the mechanism of muscle mechanotransduction has been also discovered (see Non-Patent Literature 2). Furthermore, the development of a new therapeutic method for vascular-related diseases targeting the extracellular matrix involved in the mechanical stress response in blood vessels has been also underway (see Non-Patent Literature 3).

CITATION LIST

Non-Patent Literature

Non-Patent Literature 1: Shinzo (Heart), Vol. 47, No. 12, 2015
Non-Patent Literature 2: Seikagaku (Journal of Biochemistry), Vol. 81, No. 6, 2009, pp. 494-501
Non-Patent Literature 3: PNAS May 5, 2020, 117 (18) 9896-9905

SUMMARY OF INVENTION

Technical Problem

The present invention has been made under such circumstances, and an object of the present invention is to provide a new method for evaluating and/or screening an excellent healthcare material or pharmaceutical product based on a new concept.

Solution to Problem

As a result of diligent research to solve the above problem, the present inventors discovered that a "homeostatic state of tension" (tensional homeostasis) present in the skin controls skin functionality through specific mechanical stress signals. Although transient tensile load induced by external forces is known to control cellular functionality in previous research results, the present inventors found that a continuous "tensional homeostasis", which is a state close to that of a living body, directly controls skin function for the first time. Based on these findings, the present inventors have developed a method for evaluating and/or screening a healthcare material, a pharmaceutical product, and a device based on a new concept.

Advantageous Effects of Invention

The method for evaluating and/or screening a control agent for tissue morphology and/or tissue function according to an embodiment of the present invention can identify a healthcare material or a pharmaceutical material that can transmit, to cells constituting tissues, a signal equivalent to a signal produced by mechanical stress due to continuous tensional homeostasis, which a living body experiences in the normal state. A material to be found by the method according to an embodiment of the present invention can appropriately control the tissue morphology or tissue function of a living body and thus can be expected to be effective for symptoms caused by reduced mechanical stress. The material is useful for treating, for example, deterioration in aesthetic appearance due to aging, such as wrinkles, sagging, blotches, reduced transparency, and enlarged pores in the skin; skin fibrosis, such as a scar, striae gravidarum, and keloid; and epithelial cell carcinoma.

BRIEF DESCRIPTION OF DRAWINGS

FIG. 14 is a series of images illustrating collagen fiber formation promoting effect of a mechanical stress signal promotion material.

DESCRIPTION OF EMBODIMENTS

Figure 1:
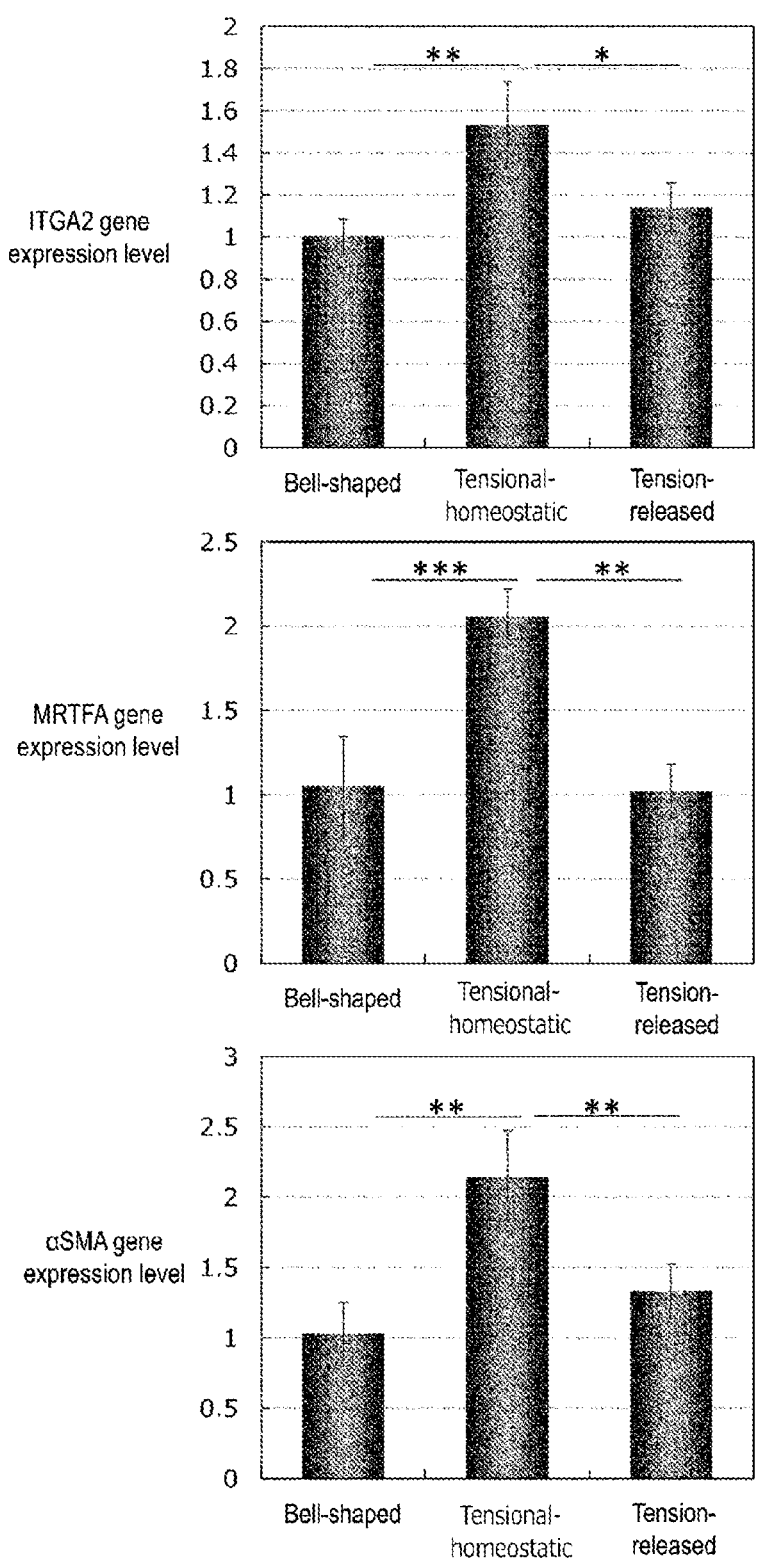
FIG. 1 is a series of graphs showing gene expression changes of mechanical stress signal molecules by tension homeostatic stimulation (Dunnett's Test *: $P<0.05$, : $P<0.01$, *: $P<0.001$).

Embodiments of the present invention will be described below. The terminology used in the present specification is interpreted to have the meaning commonly used in the art unless otherwise mentioned.

Method for evaluating and/or screening a control agent for tissue morphology and/or tissue function A method for evaluating and/or screening a control agent for tissue morphology and/or tissue function according to an embodiment of the present invention is characterized by including:

(i) applying a test substance to a tissue or cell capable of expressing a mechanical stress signaling molecule; and (ii) evaluating expression, activity, or intracellular localization of the mechanical stress signaling molecule in the tissue or cell. The method according to an embodiment of the present invention preferably further includes (iii) evaluating and/or screening a test substance that can be used as a control agent for tissue morphology and/or tissue function based on a result of step (ii) above. The method according to an embodiment of the present invention can identify a healthcare material or a pharmaceutical material that can transmit, to cells constituting tissues, a signal equivalent to a signal produced by mechanical stress due to continuous tensional homeostasis, which a living body experiences in the normal state.

The "mechanical stress" refers to mechanical stimulation, such as stretch or pressure, applied to tissues or cells. The mechanical stress is an important parameter in various aspects, such as fetal development, advancing age/aging, metabolism, and maintenance of circulatory and locomotive organs. The organs receiving strong mechanical stress in a living body include locomotive organs, such as skeletal muscles and bones; circulatory system, such as heart and blood vessels; and skin. In the tissues of these organs, an increase or decrease in mechanical stress is considered to cause significant changes in their development and structural maintenance.

The "mechanical stress signaling molecule" refers to a stretch ion channel, integrin, and the like, which are activated when a tissue or cell receives mechanical stress, and a molecule that is present downstream of them and transmits a signal from them. Examples of the mechanical stress signaling molecule that is activated when mechanical stress is applied to skin include YAP/TAZ, glycocalyx, lipid raft/caveolin-1, cell adhesion structures (ITGA2, desmosome, hemidesmosome, and cadherin), ion channels (CaSR/TRP/Piezo), MRTFA, and Rho/ROCK-associated molecules (ACTA2 (αSMA)). Among these, from the viewpoint of improving the efficiency of the method according to an embodiment of the present invention, the mechanical stress signaling molecule is preferably MRTFA or ACTA2 (αSMA) and particularly preferably MRTFA.

The "a control agent for tissue morphology and/or tissue function" refers to an agent that controls tissue morphology and/or tissue function. The agent that controls tissue morphology and/or tissue function varies depending on the tissue. Examples of an agent that controls tissue morphology in the case of skin (a control agent for skin morphology) can include agents that can control firmness, texture, or the like of the skin or can ameliorate/inhibit wrinkles, sagging, or the like. In addition, examples of an agent that controls tissue function in the case of skin (a control agent for skin function) can include agents that can improve turnover promotion, moisturization function, or barrier function of skin. Examples of the control agent for the tissue morphology and/or tissue function in an embodiment of the present invention more specifically include control agents for skin morphology, control agents for skin function, agents for preventing or ameliorating skin wrinkles/sagging, agents for preventing or ameliorating decrease in skin firmness/looseness, skin barrier function improving agents, control agents for dermis ECM formation, control agents for collagen fiber formation, skin-whitening agents, skin color-improving agents, skin texture improving agents, hair restorers/hair growth inhibitors, and acne therapeutic agents. These can be suitably used in cosmetics for anti-aging or skin care or therapeutic agents for skin diseases.

The method for evaluating and/or screening a control agent for tissue morphology and/or tissue function according to an embodiment of the present invention will be described for each step below.

(i) Application of Test Substance to Tissue or Cell Capable of Expressing Mechanical Stress Signaling Molecule In the present step, a test substance and a tissue or cell capable of expressing a mechanical stress signaling molecule are prepared, and the test substance is applied to the tissue or cell.

The tissue or cell used in the present step is not particularly limited as long as the tissue or cell can express the mechanical stress signaling molecule. Examples include a tissue or cell that is isolated from a mammal and can express the mechanical stress signaling molecule or its gene, or a culture of the tissue or cell. Specifically, examples include skin tissues, epidermal tissues, dermis tissues, epidermal cells (such as epidermal keratinocytes), and dermis cells (such as dermis fibroblasts) taken from a mammal, their cultures (including established cell lines), and skin equivalent models composed of any of these. Of these, from the viewpoint of convenience, epidermal keratinocytes or dermis fibroblasts are preferred. In addition, from the viewpoint of obtaining a result closer to the actual skin, a skin equivalent model is preferred, and a skin equivalent model composed of epidermal keratinocytes and dermis fibroblasts is more preferred. Such a skin equivalent may be a commercially available skin equivalent known in the art and is not particularly limited. Preferred examples include those constructed by preparing an artificial dermis by dispersing and seeding normal human dermis fibroblasts in a collagen gel or the like and solidifying, and seeding normal human epidermal keratinocytes on the artificial dermis and culturing in a gas phase. Furthermore, examples of the state of the skin equivalent include: a tensional homeostatic skin equivalent model, in which an artificial dermis is fixed at its circumference in a culture vessel to reproduce the state of balanced intercellular tension similar to the natural skin; and a bell-shaped skin equivalent, in which the tension is released by suspension culture of an artificial dermis. The tensional homeostatic skin equivalent model is particularly preferred.

The tissue or cell used in the present step may be a tissue or cell of a mammal, or its culture, wherein the tissue or cell of a mammal is genetically modified to express the mechanical stress signaling molecule or its gene. The genetically modified mammalian tissue or cell, and its culture can be made, for example, by introducing a gene encoding the mechanical stress signaling molecule into any tissue or cell of a mammal, and transforming the tissue or cell to express the mechanical stress signaling molecule or to strengthen the expression of the mechanical stress signaling molecule. Alternatively, cells in which a construct is introduced, or their culture, can also be used, the construct being made by fusing a reporter gene, such as luciferase, downstream of the promoter region of the gene of the mechanical stress signaling molecule. A method known in the art to introduce the gene or construct into the cell can be used, and examples include vector introductions by electroporation or lipofection.

Examples of the mammal from which the tissue or cell used in the present step is derived include humans, mice, rats, hamsters, rabbits, pigs, and monkeys. Of these, the tissue or cell derive from a human is preferred.

The test substance in the present step is not particularly limited. The test substance may be a naturally occurring substance or may be a substance synthesized by a chemical or biological method or the like. In addition, the test substance may be a small molecule compound, a peptide, a protein, a nucleic acid, or an extract from a natural product, such as a plant extract; a mixture of these; or a composition containing these.

The application of the test substance to a tissue or cell capable of expressing a mechanical stress signaling molecule can be performed, for example, by adding the test substance into a medium to give a predetermined concentration in advance and then seeding the tissue or cell to the medium; or by adding the test substance to a medium in which the tissue or cell has been seeded, to give a predetermined concentration. The tissue or cell after application of the test substance is preferably cultured under common conditions, for example, in the case of epidermal keratinocytes, dermis fibroblasts, or a skin equivalent model, at 25 to 37° C. for approximately from 8 to 240 hours and preferably approximately from 24 to 120 hours.

The concentration of the test substance to be added may be set at an appropriate concentration according to the type of the test substance. The concentration of the test substance is, for example, in a range of 0.00001 to 10% (w/v).

For the medium for culturing the tissue or cell, a medium appropriate for the tissue or cell to be used can be appropriately selected, and examples include, but are not limited to, a DMEM medium, for example, containing or not containing 10% fetal bovine serum (FBS).

(ii) Evaluation of Expression, Activity, or Intracellular Localization of Mechanical Stress Signaling Molecule in Tissue or Cell Above In the present step, to perform evaluation/screening of the test substance applied in step (i) above, a change in expression, activity, or intracellular localization of the mechanical stress signaling molecule in the tissue or cell by the test substance is measured.

The expression of the mechanical stress signaling molecule may be an expression level of a gene encoding the mechanical stress signaling molecule or may be an expression level of the mechanical stress signaling molecule (protein) itself. Measurement of the expression level of the gene or the expression level of the protein can be performed according to a known method. For detecting the expression level of the gene through an mRNA level, for example, total RNA is extracted from cells, then mRNA transcribed from the mechanical stress signaling molecular gene can be detected and quantified using a real-time RT-PCR method, an RNA degrading enzyme protection assay method, a DNA array method, a Northern blot analysis method, or the like. Measurement of the expression level of the protein can be performed by a common immunoassay method, such as, for example, an RIA method, ELISA, a bioassay method, or Western blot. Western blot is inexpensive and convenient, and thus is desirable.

The measurement of the activity of the mechanical stress signaling molecule can be performed by an appropriate method for each molecule. For example, the measurement can be performed by quantifying the level of RNA transcription by an RT-PCR, detecting phosphorylation of a specific molecule by Western blotting, or detecting the molecular activity by detecting a fluorescence/emission quantity resulting from introduction of a reporter gene.

The intracellular localization of the mechanical stress signaling molecule can be determined by performing immunohistochemical staining using an antibody that specifically binds to each molecule, or the like. An effect of the test substance (such as nuclear import of a transcription factor, a polymerization level of cytoskeletal molecules, and a change in the integrin subtype on the cell membrane) can be determined by image analysis or the like in comparison with a control.

(iii) Evaluation/Screening of Test Substance that can be Used as a Control Agent for Tissue Morphology and/or Tissue Function Based on Result of Step (ii) Above In the present step, the test substance is evaluated for whether the test substance can be used as a control agent for tissue morphology and/or tissue function and selected based on a measurement result of a change in expression, activity, or intracellular localization of the mechanical stress signaling molecule in the tissue or cell by the test substance in step (ii) above.

In the evaluation of whether the test substance can be used as a control agent for tissue morphology and/or tissue function and the selection of the test substance in the present step, the expression, activity, or intracellular localization of the mechanical stress signaling molecule in the tissue or cell to which the test substance is applied is compared with a control group. Examples of the control group include those having the same tissue or cell as that of the test group but with no test substance applied or only a solvent of the test substance applied. The expression, activity, or intracellular localization of the mechanical stress signaling molecule in the control group can also be measured/detected in the same manner as described in step (ii).

When the expression or activity level of the mechanical stress signaling molecule or its gene in the test group is higher than that in the control group, the test substance is selected as a substance that enhances the expression or activity level of the mechanical stress signaling molecule or its gene. For example, when the expression or activity level in the test group shows a statistically significant increase relative to the expression or activity level in the control group, the test substance is selected as a substance that enhances the expression or activity level of the mechanical stress signaling molecule or its gene. Specifically, when the expression or activity level in the control group is defined as 100%, and the expression or activity level in the test group is 110% or higher, preferably 130% or higher, or more preferably 150% or higher, the test substance can be selected as a substance that enhances the expression or activity level of the mechanical stress signaling molecule or its gene. The selected test substance can be selected as a control agent for skin morphology, a control agent for skin function, an agent for preventing or ameliorating skin wrinkles/sagging, an agent for preventing or ameliorating decrease in skin firmness/looseness, an improving agent for skin barrier function, a control agent for dermis ECM formation or a control agent for collagen fiber formation, a skin-whitening agent, a skin color-improving agent, an improving agent for skin texture, a hair restorer/hair growth inhibitor, or an acne therapeutic agent, or as their candidate substance. These substances are suitably used as cosmetics, skin care products, and the like for the purpose of anti-aging.

When the expression or activity level of the mechanical stress signaling molecule or its gene in the test group is lower than that in the control group, the test substance is selected as a substance that reduces the expression or activity level of the mechanical stress signaling molecule or its gene. For example, when the expression or activity level in the test group shows a statistically significant decrease relative to the expression or activity level in the control group, the test substance is selected as a substance that reduces the expression or activity level of the mechanical stress signaling molecule or its gene. In addition, when the expression or activity level in the control group is defined as 100%, and the expression or activity level in the test group is 90% or lower, preferably 70% or lower, or more preferably 50% or lower, the test substance is selected as a substance that reduces the expression or activity level of the mechanical stress signaling molecule or its gene. The selected test substance can be selected as a control agent for skin morphology, a control agent for skin function, a control agent for dermis ECM formation, or a control agent for collagen fiber formation, or as their candidate substance. These substances are effective, for example, in the treatment of skin fibrosis, such as a scar, striae gravidarum, and keloid; and epithelial cell carcinoma.

In the method according to an embodiment of the present invention, the substance selected by the above procedure may be subjected to further screening as necessary. The test substance selected as a substance that enhances or reduces the expression or activity level of the mechanical stress signaling molecule or its gene or a substance that changes the intracellular localization in step (iii) above is reported as a candidate substance for the agent according to an embodiment of the present invention. Then, screening for a superior test substance can be carried out by administering these candidate substances to a tissue or cell (a skin tissue, an epidermal tissue, a dermis tissue, epidermal keratinocytes, dermis fibroblasts, or their cultures, or a skin equivalent model composed of any of these) capable of expressing the mechanical stress signaling molecule, then determining and confirming an ECM synthesis function, a type I collagen synthesis function, an epidermal keratinocyte ability proliferation-promoting function and a turnover-promoting function resulting therefrom, a function of promoting proliferation of epidermal keratinocytes, a function of maintaining the orientation of collagen fibers aligned in the same horizontal direction as the tension direction, or the like, and comparing with the control group as necessary. The ECM synthesis function, the type I collagen synthesis function, the epidermal keratinocyte ability proliferation-promoting function and the turnover-promoting function resulting therefrom, the function of promoting the proliferation of epidermal keratinocytes, and the function of maintaining the orientation of collagen fibers aligned in the same horizontal direction as the tension direction can be measured by known methods, such as RT-PCR, microarray, immunoassay, Western blotting, and immunohistochemical staining.

Method for evaluating device for tissue morphology and/or tissue function control A method for evaluating a device for tissue morphology and/or tissue function control according to an embodiment of the present invention is characterized by including:

(i) applying a mechanical stress load by a test device to a tissue or cell capable of expressing a mechanical stress signaling molecule; and (ii) evaluating expression, activity, or intracellular localization of the mechanical stress signaling molecule in the tissue or cell. The method according to an embodiment of the present invention preferably further includes (iii) evaluating whether the test device can be used as a device for tissue morphology and/or tissue function control based on a result of step (ii) above. The method according to an embodiment of the present invention can appropriately evaluate a device for health care or a device for medical use that can transmit, to cells constituting tissues, a signal equivalent to mechanical stress due to continuous tensional homeostasis, which a living body experiences in the normal state.

The "device for tissue morphology and/or tissue function" refers to a device, a machine, equipment, or the like that is configured to apply mechanical stress, specifically to apply pressure stimulation, ultrasonic stimulation, or any other physical stimulation to a tissue, to control tissue morphology and/or tissue function. The device for appropriately controlling tissue morphology and/or tissue function may vary depending on the tissue to which the device is applied. Examples in the case of skin can include devices that is configured to control firmness, texture, or the like of the skin or can ameliorate/inhibit wrinkles, sagging, or the like. In addition, examples of a device that is configured to control tissue function in the case of skin can include devices that can improve turnover promotion, moisturization function, or barrier function of skin. The device for tissue morphology and/or tissue function control in an embodiment of the present invention is more specifically a device that can be expected to provide skin morphology control, skin function control, prevention or amelioration of skin wrinkles/sagging, prevention or amelioration of decrease in skin firmness/looseness, skin barrier function improvement, dermis ECM formation control, collagen fiber formation control, skin whitening, skin color improvement, skin texture improvement, hair restoration/hair growth inhibition, acne treatment, or the like. These can be suitably used for the purpose of anti-aging, skin care, treatment of skin diseases, or the like.

The method for evaluating a device for tissue morphology and/or tissue function control according to an embodiment of the present invention will be described for each step below.

(i) Application of Mechanical Stress Load by Test Device to Tissue or Cell Capable of Expressing Mechanical Stress Signaling Molecule In the present step, a test device and a tissue or cell capable of expressing a mechanical stress signaling molecule are prepared, and a mechanical stress load is applied by the test device to the tissue or cell.

For the description of the tissue or cell to be used in the present step, the description in the section of the method for evaluating and/or screening a control agent for tissue morphology and/or tissue function can be applied as it is.

The test device in the present step is not particularly limited and refers to a device in general that can apply pressure stimulation, ultrasonic stimulation, or other physical stimulation to the skin.

The application of a mechanical stress load by the test device to a tissue or cell capable of expressing a mechanical stress signaling molecule is performed according to specifications of each device.

(ii) Evaluation of Expression, Activity, or Intracellular Localization of Mechanical Stress Signaling Molecule in Tissue or Cell Above In the present step, to perform evaluation of (the mechanical stress load by) the test device applied in step (i) above, a change in expression, activity, or intracellular localization of the mechanical stress signaling molecule in the tissue or cell by the mechanical stress load applied by the test device is measured. For the description of the expression, activity, and intracellular localization of the mechanical stress signaling molecule, the description in the section of the method for evaluating and/or screening a control agent for tissue morphology and/or tissue function can be applied as it is.

(iii) Evaluation of Whether Test Device Above can be Used as Device for Tissue Morphology and/or Tissue Function Control In the present step, the test device is evaluated for whether the test device is effective as a device for tissue morphology and/or tissue function control based on a measurement result of a change in expression, activity, or intracellular localization of the mechanical stress signaling molecule in the tissue or cell by the mechanical stress load applied by the test device in step (ii) above.

In the evaluation of whether the test substance can be used as a device for tissue morphology and/or tissue function control in the present step, the expression, activity, or intracellular localization of the mechanical stress signaling molecule in the tissue or cell to which the mechanical stress load is applied by the device is compared with a control group. Examples of the control group include those in which the mechanical stress load is not applied to the same tissue or cell as that of the test group. The expression, activity, or intracellular localization of the mechanical stress signaling molecule in the control group can also be measured/detected in the same manner as described in step (ii).

When the expression or activity level of the mechanical stress signaling molecule or its gene in the test group is higher than that in the control group, the test device (or the condition of the mechanical stress load applied by the device) is selected as a device (or the condition) that enhances the expression or activity level of the mechanical stress signaling molecule or its gene. For example, when the expression or activity level in the test group shows a statistically significant increase relative to the expression or activity level in the control group, the test device (or the condition) is selected as a device (or the condition) that enhances the expression or activity level of the mechanical stress signaling molecule or its gene. Specifically, when the expression or activity level in the control group is defined as 100%, and the expression or activity level in the test group is 110% or higher, preferably 130% or higher, or more preferably 150% or higher, the test device (or the condition) can be selected as a device (or the condition) that enhances the expression or activity level of the mechanical stress signaling molecule or its gene. The evaluated test device can be suitably used for skin morphology control, skin function control, prevention or amelioration of skin wrinkles/sagging, prevention or amelioration of decrease in skin firmness/looseness, skin barrier function improvement, dermis ECM formation control or collagen fiber formation control, skin whitening, skin color improvement, skin texture improvement, hair restoration/hair growth inhibition, acne treatment, or the like. These devices (or the conditions) can be used for cosmetic purposes, such as anti-aging and skin care, and for medical purposes, such as acne treatment.

When the expression or activity level of the mechanical stress signaling molecule or its gene in the test group is lower than that in the control group, the test device (or the condition of the mechanical stress load by the device) is selected as a device (or the condition) that reduces the expression or activity level of the mechanical stress signaling molecule or its gene. For example, when the expression or activity level in the test group shows a statistically significant decrease relative to the expression or activity level in the control group, the test device (or the condition) is selected as a device (or the condition) that reduces the expression or activity level of the mechanical stress signaling molecule or its gene. In addition, when the expression or activity level in the control group is defined as 100%, and the expression or activity level in the test group is 90% or lower, preferably 70% or lower, or more preferably 50% or lower, the test device (or the condition) is selected as a device (or the condition) that reduces the expression or activity level of the mechanical stress signaling molecule or its gene. The evaluated device (or the condition) can be suitably used for cosmetic purposes, such as skin morphology control, skin function control, dermis ECM formation control, and collagen fiber formation control. In addition, these devices (or the conditions) can also be suitably used for medical purposes, for example, such as treatment of skin fibrosis, such as a scar, striae gravidarum, and keloid; and epithelial cell carcinoma.

In the method according to an embodiment of the present invention, the device evaluated by the above procedure may be subjected to further evaluation as necessary. A superior device (or condition above) can be evaluated/screened by applying the device (or the condition) that enhances or reduces the expression or activity level of the mechanical stress signaling molecule or its gene or the device (or the condition) evaluated as a device (or the condition) that changes the intracellular localization in step (iii) above, to a tissue or cell (a skin tissue, an epidermal tissue, a dermis tissue, epidermal keratinocytes, dermis fibroblasts, or their cultures, or a skin equivalent model composed of any of these) capable of expressing the mechanical stress signaling molecule, then determining and confirming an ECM synthesis function, a type I collagen synthesis function, an epidermal keratinocyte ability proliferation-promoting function and a turnover-promoting function resulting therefrom, a function of promoting proliferation of epidermal keratinocytes, a function of maintaining the orientation of collagen fibers aligned in the same horizontal direction as the tension direction, or the like, and comparing with the control group as necessary. The ECM synthesis function, the type I collagen synthesis function, the epidermal keratinocyte ability proliferation-promoting function and the turnover-promoting function resulting therefrom, the function of promoting the proliferation of epidermal keratinocytes, and the function of maintaining the orientation of collagen fibers aligned in the same horizontal direction as the tension direction can be measured by known methods, such as RT-PCR, microarray, immunoassay, Western blotting, and immunohistochemical staining.

Applications of Embodiments of the Present Invention

As described above, a control agent for skin morphology, a control agent for skin function, an agent for preventing or ameliorating skin wrinkles/sagging, an agent for preventing or ameliorating decrease in skin firmness/looseness, an improving agent for skin barrier function, a control agent for dermis ECM formation, a control agent for collagen fiber formation, a skin-whitening agent, a skin color-improving agent, an improving agent for skin texture, or a hair restorer/hair growth inhibitor selected by the evaluation/screening method according to an embodiment of the present invention can be suitably used in cosmetics, quasi-pharmaceutical products, oral agents requiring anti-aging (prevention/amelioration of wrinkles, sagging, blotches, reduced transparency, enlarged pores in the skin, or the like) or skin care, such as moisturization, skin whitening, or promotion of skin turnover. In addition, the selected agent can also be suitably used for pharmaceutical agents, such as therapeutic agents for skin fibrosis, such as a scar, striae gravidarum, and keloid; therapeutic agents for epithelial cell carcinoma; and acne therapeutic agents.

In addition, as described above, a device for skin morphology control, a device for skin function control, a device for preventing or ameliorating skin wrinkles/sagging, a device for preventing or ameliorating decrease in skin firmness/looseness, a device for improving skin barrier function, a device for controlling dermis ECM formation, a device for controlling collagen fiber formation, skin-whitening, improving skin color, improving skin texture, or hair restoration/hair growth inhibition evaluated/selected by the evaluation method according to an embodiment of the present invention can be suitably used as a health care device for a beauty device or the like for the purpose of anti-aging (prevention/amelioration of wrinkles, sagging, blotches, reduced transparency, enlarged pores in the skin, or the like) or skin care, such as moisturization, skin whitening, or promoting skin turnover. Furthermore, the device can also be suitably used as a medical device for treatment of skin fibrosis, such as a scar, striae gravidarum, and keloid; epithelial cell carcinoma; and acne.

Use of the agent selected by the evaluation/screening method according to an embodiment of the present invention in combination with a health care device, such as a beauty care device, or a practice method, such as massage or relaxation, can further increase the effect. In addition, the concept in the screening method and evaluation method according to an embodiment of the present invention can also be applied in the development of the practice method. That is, also for the practice method, those that enhance or reduce an expression or activity level of a mechanical stress signaling molecule or its gene in a target cell or changes intracellular localization toward preferred direction can be developed.

EXAMPLES

The present invention will be described in further detail by examples below, but the present invention is in no way limited by these examples.

Example 1: Expression and Localization Change of Mechanical Stress Signal Molecules by Tension Homeostatic Stimulation Normal human dermis fibroblasts (Kurabo Industries Ltd.) were expanded and cultured using a DMEM medium (Thermo Fisher Scientific Inc.) containing 10 ng/mL bFGF (PeproTech, Inc.), 10% fetal bovine serum, and 1% penicillin/streptomycin, and using a tissue culture-coated Petri dish. Normal human epidermal keratinocytes (Kurabo Industries Ltd.) were expanded and cultured using a Humedia-KG2 medium (Kurabo Industries Ltd.) and using a tissue culture-coated Petri dish. On an artificial dermis formed by dispersing and seeding normal human dermis fibroblasts in a collagen gel (KOKEN Co., Ltd.) and solidifying, normal human epidermal keratinocytes were seeded and cultured in a gas phase using an artificial skin maintenance medium containing 10% fetal bovine serum, 1% penicillin/streptomycin, 5 μg/mL insulin (FUJIFILM Wako Pure Chemical Corporation), 1 mM magnesium ascorbyl phosphate (FUJIFILM Wako Pure Chemical Corporation), 10 ng/mL bFGF (PeproTech, Inc.), and 1 μM hydrocortisone (FUJIFILM Wako Pure Chemical Corporation), and a skin equivalent was constructed. For skin equivalents, the following were constructed: a bell-shaped skin equivalent, in which the tension was released by suspension culture of the artificial dermis, according to a common method for constructing a skin equivalent in the art; and a tensional homeostatic skin equivalent model, in which fixing the circumference of an artificial dermis in a culture vessel reproduced, in a skin equivalent, the state of the balanced intercellular tension similar to that of the natural skin, were constructed. Furthermore, 5 days after the gas phase culture, the tensional homeostatic skin equivalent model was separated from the culture vessel to release the tension, and a tension-released skin equivalent model was prepared accordingly.

From the three skin equivalents of: the bell-shaped skin equivalent; the tensional homeostatic skin equivalent model; and the tension-released skin equivalent model, tissues were collected on day 7 of the gas phase culture. From a portion of the collected tissue, total RNA was immediately recovered using RNeasy Plus Mini Kit (QIAGEN K.K.) according to the attached protocol. The cDNA was reverse-transcribed from the obtained total RNA using SuperScript VILO (Thermo Fisher Scientific Inc.) according to the attached protocol. Real-time PCRs of the mechanical stress signaling genes, that is, ITGA2, MRTFA, and ACTA2 (αSMA) were performed with an Applied Biosystems QuantStudio 12K Flex (Thermo Fisher Scientific Inc.) using an SYBR Premix Ex Taq II or TaqMan (trade name) Gene Expression Assay system (Thermo Fisher Scientific Inc.). The measured expression value of each gene was corrected by the ΔΔCT method by setting GAPDH as the endogenous gene expression control.

Furthermore, a portion of the collected tissue was immediately fixed in 4% paraformaldehyde phosphate buffer, a paraffin section was prepared by a common method, and immunohistochemical staining for each mechanical stress signaling molecule below was performed by the following procedure.

ITGA2

Immunohistochemical staining was performed using a rabbit anti-human ITGA2 antibody (Abcam. plc) and an Alexa Fluor 594-labeled anti-rabbit IgG antibody (Thermo Fisher Scientific Inc.). The nuclei of the stained tissue were stained using Hoechst 33342 (Thermo Fisher Scientific Inc.), and the nuclei (excitation wavelength: 350 nm, observation wavelength 470 nm) and a total level and localization of ITGA2 expression (excitation wavelength 594 nm, observation wavelength 620 nm) were observed using a confocal microscope.

MRTFA

Immunohistochemical staining was performed using a rabbit anti-human MRTFA antibody (Abcam. plc) and an Alexa Fluor 594-labeled anti-rabbit IgG antibody (Thermo Fisher Scientific Inc.). The nuclei of the stained tissue were stained using Hoechst 33342 (Thermo Fisher Scientific Inc.), and the nuclei (excitation wavelength: 350 nm, observation wavelength 470 nm) and a total level and localization of MRTFA expression (excitation wavelength 594 nm, observation wavelength 620 nm) were observed using a confocal microscope. Furthermore, the nuclear import level of MRTFA was quantitatively evaluated by calculating the average value of the fluorescence signal intensities of Alexa 594 in the Hoechst-positive nuclear region by image analysis using Image J.

αSMA

Immunohistochemical staining was performed using a rabbit anti-human αSMA antibody (Abcam. plc) and an Alexa Fluor 594-labeled anti-rabbit IgG antibody (Thermo Fisher Scientific Inc.). The nuclei of the stained tissue were stained using Hoechst 33342 (Thermo Fisher Scientific Inc.), and the nuclei (excitation wavelength: 350 nm, observation wavelength 470 nm) and a total level and localization of αSMA expression (excitation wavelength 594 nm, observation wavelength 620 nm) were observed using a confocal microscope.

FIG. 1 is a series of plots of the expression levels of the mechanical stress signaling genes in each skin equivalent model. The tensional homeostatic skin equivalent model showed statistically significantly higher gene expression levels of ITGA2, MRTFA, and ACTA2 (αSMA) compared with the other two models without tension homeostatic stimulation.

Figure 2:
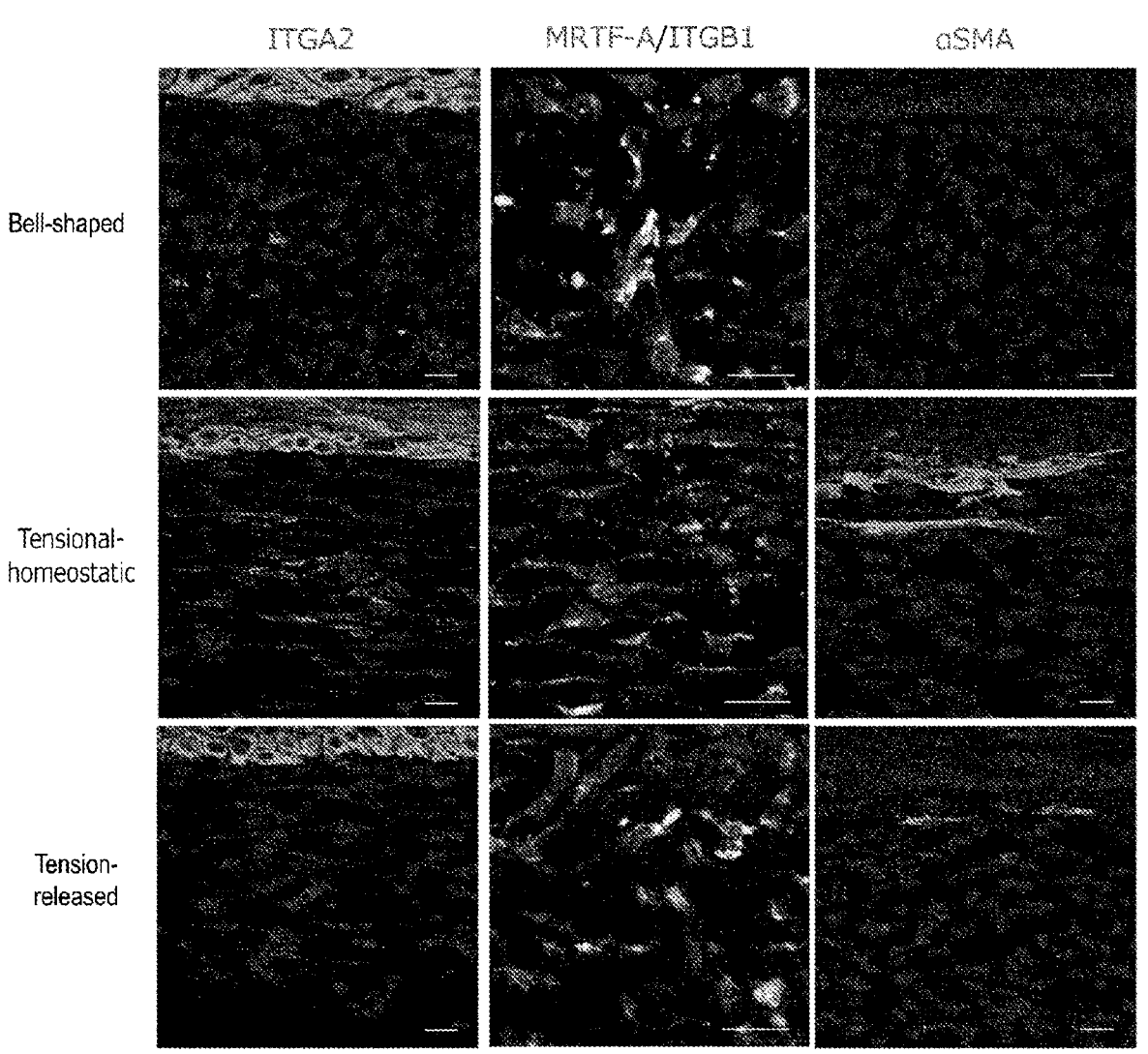
FIG. 2 is a series of images illustrating changes in expression and localization of mechanical stress signal molecules by tension homeostatic stimulation.

Immunohistochemical staining images of the mechanical stress signaling molecules in each skin equivalent model are shown in FIG. 2. In the tensional homeostatic skin equivalent model, the expression levels of ITGA2, MRTFA, and ACTA2 (αSMA) increased compared with the other two models without tension homeostatic stimulation.

Figure 3:
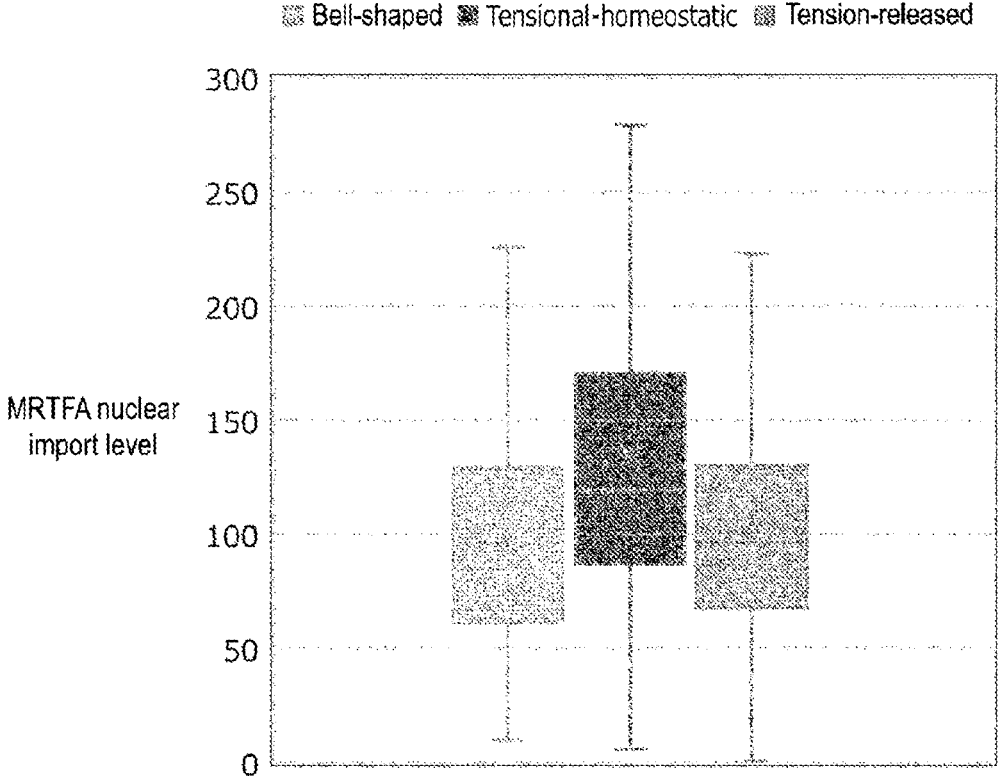
FIG. 3 is a graph showing nuclear import rates of MRTFA by tension homeostatic stimulation.

FIG. 3 is a plot of the results of the quantitative evaluation of the nuclear import level of MRTFA per cell determined by image analysis of the immunohistochemical staining image. In the tensional homeostatic skin equivalent model, statistically significantly higher nuclear import of ITGA2, MRTFA, and ACTA2 (αSMA) was observed compared with the other two models without tension homeostatic stimulation.

From the above, in the tensional homeostatic skin equivalent model reflecting the actual good skin condition, the expression of the mechanical stress signaling molecules (ITGA2, MRTFA, and ACTA2 (αSMA)) was found to be promoted compared with the other two models without tension homeostatic stimulation.

Example 2: Control of Functionality of Skin Constituent Cells by Adjustment of Tension Homeostatic Stimulation The bell-shaped skin equivalent model, the tensional homeostatic skin equivalent model, and the tension-released skin equivalent model were prepared in the same manner as in Example 1.

From the three skin equivalents of: the bell-shaped skin equivalent; the tensional homeostatic skin equivalent model; and the tension-released skin equivalent model, tissues were collected on day 7 of the gas phase culture, total RNA was recovered from each tissue, and a real-time PCR was performed in the same manner as in Example 1. The analyzed genes were COL1A1, COL1A2, FBN1, ELN, and MMP1, which are genes related to dermis function, that is, ECM synthesis function, and KGF, which is a gene related to epidermal turnover function, that is, an epidermal keratinocyte proliferation control gene. The measured expression value of each gene was corrected by the ΔΔCT method by setting GAPDH as the endogenous gene expression control.

Furthermore, a portion of the collected tissue was immediately fixed in 4% paraformaldehyde phosphate buffer, a paraffin section was prepared by a common method, and immunohistochemical staining for type I collagen, which is involved in ECM synthesis function, and Ki67, a proliferation marker of epidermal keratinocytes, was performed by the following procedure.

COL1

Immunohistochemical staining was performed using a rabbit anti-human type I collagen antibody (Abcam. plc) and an Alexa Fluor 594-labeled anti-rabbit IgG antibody (Thermo Fisher Scientific Inc.). The nuclei of the stained tissue were stained using Hoechst 33342 (Thermo Fisher Scientific Inc.), and the nuclei (excitation wavelength: 350 nm, observation wavelength 470 nm) and a total level and localization of COL1 expression (excitation wavelength 594 nm, observation wavelength 620 nm) were observed using a confocal microscope.

Immunohistochemical staining was performed using a rat anti-human ki67 antibody (Abcam. plc) and an Alexa Fluor 594-labeled anti-rat IgG antibody (Thermo Fisher Scientific Inc.). The nuclei of the stained tissue were stained using Hoechst 33342 (Thermo Fisher Scientific Inc.), and the nuclei (excitation wavelength: 350 nm, observation wavelength 470 nm) and Ki67 expression (excitation wavelength 594 nm, observation wavelength 620 nm) were observed using a confocal microscope. Furthermore, the number of Ki67-positive cells was visually counted.

Moreover, a portion of the collected tissue was immediately fixed in 4% paraformaldehyde phosphate buffer, a frozen section was prepared by a common method, and a three-dimensional structure image of type I collagen fiber was captured according to the method of Lynch, B. et al. by second harmonic generation imaging. The orientation of the fibroblast nuclei was evaluated by elliptical approximation of the fluorescence image of the nuclei using Image J and measuring the slope of the principal axis of the approximated ellipse. In addition, the orientation of type I collagen in the dermis was evaluated by the two-dimensional fast Fourier transform analysis using the FFT function and the Oval profile plug-in of Image J.

Figure 4:
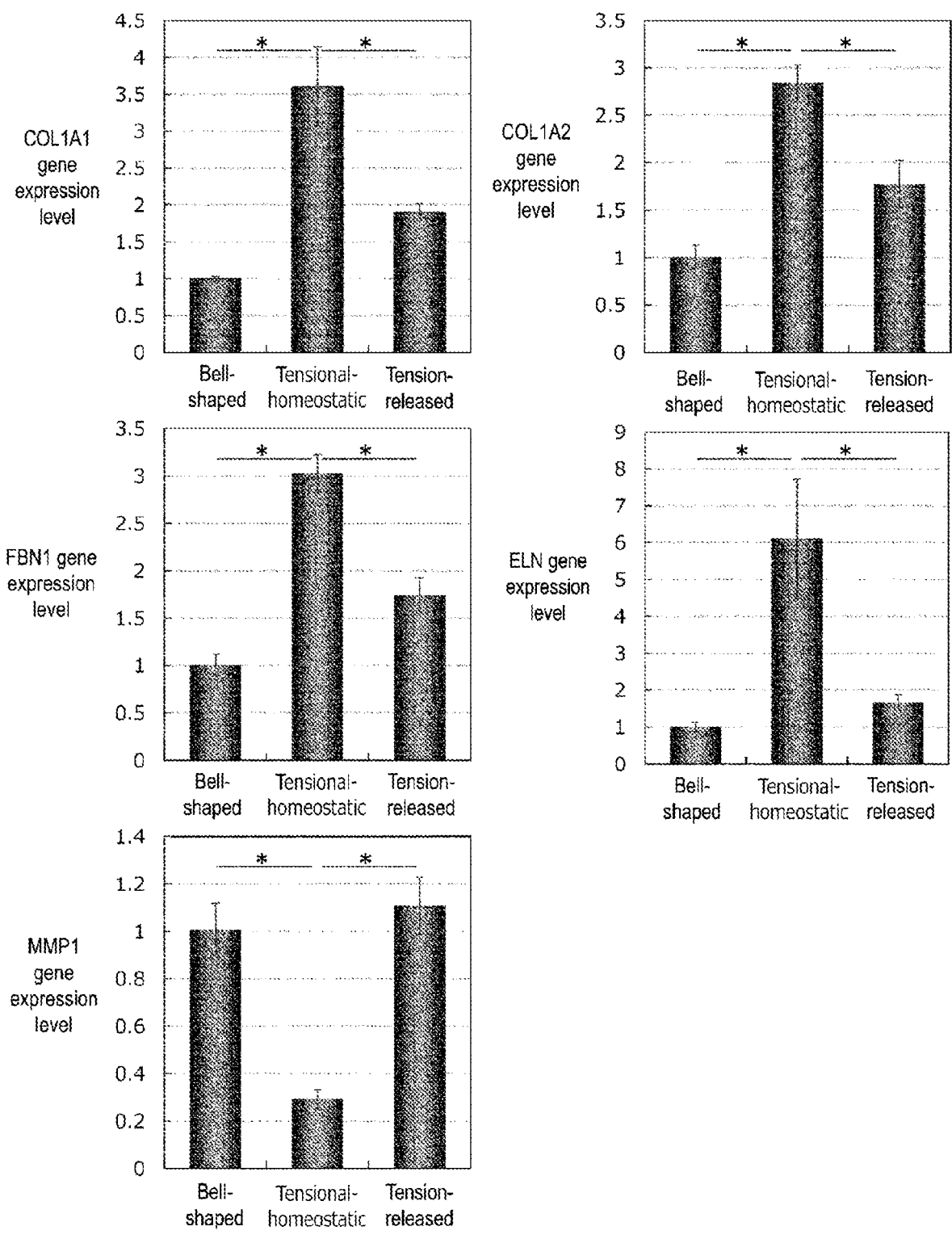
FIG. 4 is a series of graphs showing changes in expression levels of genes related to ECM synthesis by tension homeostatic stimulation (Dunnett's Test *: $P<0.001$).

FIG. 4 is a series of plots of the expression levels of the genes related to the function of the dermis, that is, the ECM synthesis function in each skin equivalent model. In the Tensional homeostatic skin model in which tension homeostatic stimulation was applied, the expression of COL1A1, COL1A2, FBN1, and ELN, genes encoding constituent fibrous proteins of ECM, increased, and the expression of MMP1, a collagen-degrading enzyme, decreased relative to those in the bell-shaped skin equivalent without tension, indicating an improved ECM synthesis function by the tension homeostatic stimulation. In addition, in the tension-released model, the expression of COL1A1, COL1A2, FBN1, and ELN, genes encoding constituent fibrous proteins of ECM, decreased, and the expression of MMP1, a collagen-degrading enzyme, increased compared with the tensional homeostatic model, indicating a decreased ECM synthesis function by the release of tensional homeostasis.

Figure 5:
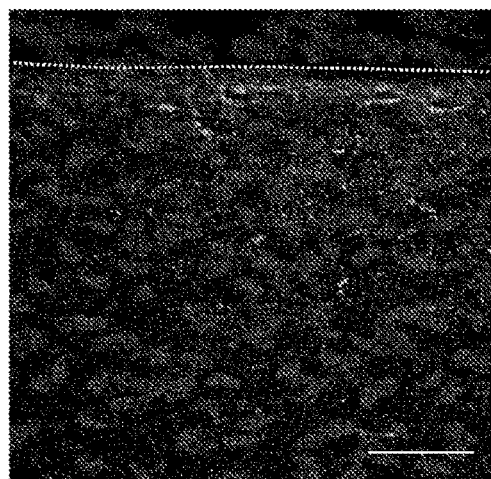
FIG. 5 is a series of images illustrating changes in formation of type I collagen fibers by tension homeostatic stimulation.
Figure 5:
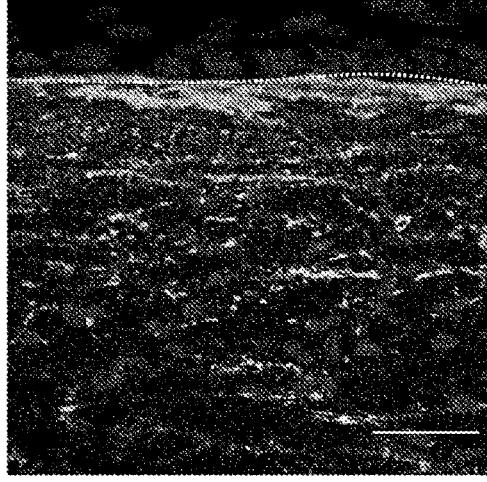
Figure 5:
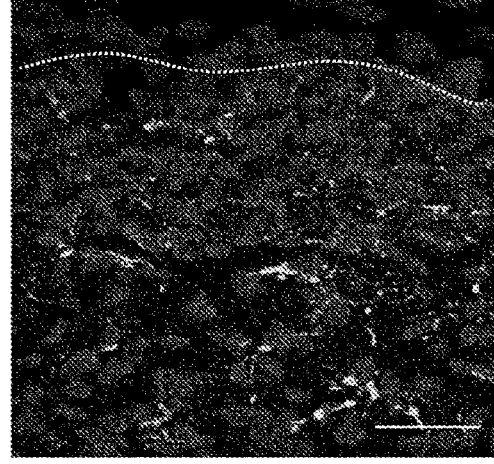

The immunohistochemical staining images of type I collagen in each skin equivalent model are shown in FIG. 5. In the Tensional homeostatic skin model in which tension homeostatic stimulation was applied, the expression of type I collagen increased relative to that in the bell-shaped skin equivalent without tension, indicating an improved type I collagen synthesis function by the tension homeostatic stimulation. In addition, in the tension-released model, the expression of type I collagen decreased compared with the tensional homeostatic model, indicating a decreased type I collagen synthesis function by the release of tensional homeostasis.

Figure 6:
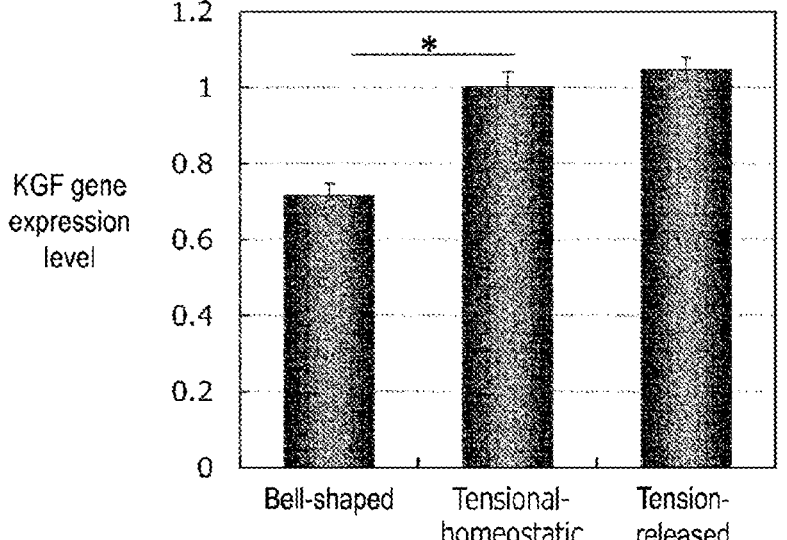
FIG. 6 is a graph showing changes in KGF gene expression levels by tension homeostatic stimulation (Dunnett's Test *: $P<0.001$).

FIG. 6 is a plot of the turnover function of the epidermis, that is, the expression levels of KGF, an epidermal keratinocyte proliferation control gene in each skin equivalent model. In the Tensional-homeostatic skin model in which tension homeostatic stimulation was applied, the expression of KGF increased relative to that in the bell-shaped skin equivalent without tension, suggesting an epidermal keratinocyte proliferation promoting effect by the tension homeostatic stimulation and the turnover promoting effect resulting therefrom.

Figure 7:
FIG. 7 is a series of images illustrating Ki67-positive cell distribution by tension homeostatic stimulation.
Figure 7:
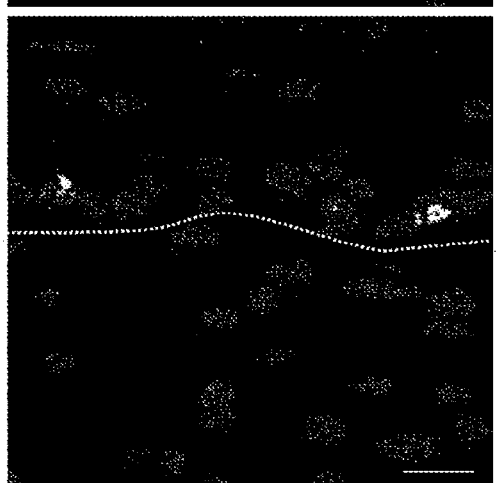
Figure 7:
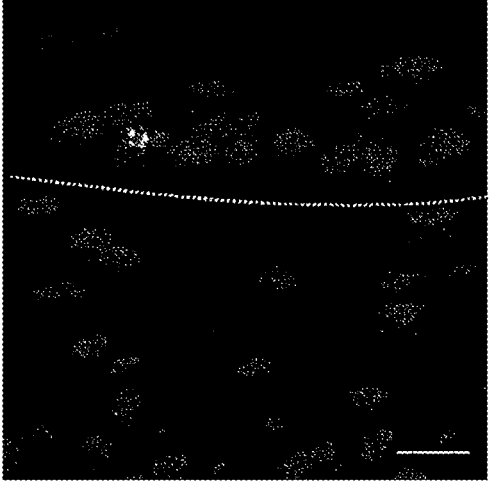
Figure 8:
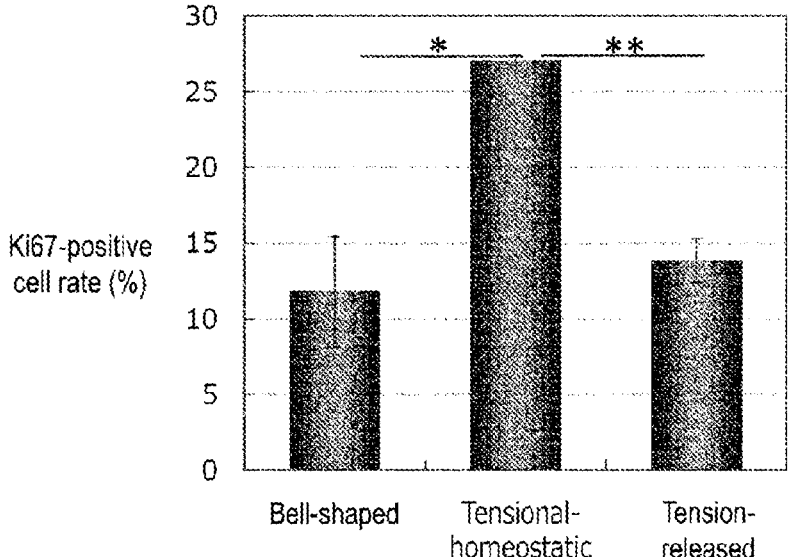
FIG. 8 is a graph showing changes in Ki67-positive proliferative cell rates of epidermal keratinocytes by tension homeostatic stimulation (Dunnett's Test *: $p<0.01$, **: $p<0.001$).

The immunohistochemical staining images of the proliferative cell marker Ki67 in each skin equivalent model are shown in FIG. 7. In addition, the counting results of Ki67-positive cell counts were plotted in FIG. 8. In the Tensional homeostatic skin model in which tension homeostatic stimulation was applied, the number of cells expressing Ki67 increased relative to that in the bell-shaped skin equivalent without tension, indicating a proliferation promoting effect on epidermal keratinocytes by the tension homeostatic stimulation. In addition, in the tension-released model, the Ki67-positive cell counts decreased compared with the tensional homeostatic model, indicating an inhibitory effect on proliferation of epidermal keratinocytes by the release of tensional homeostasis.

Figure 9:
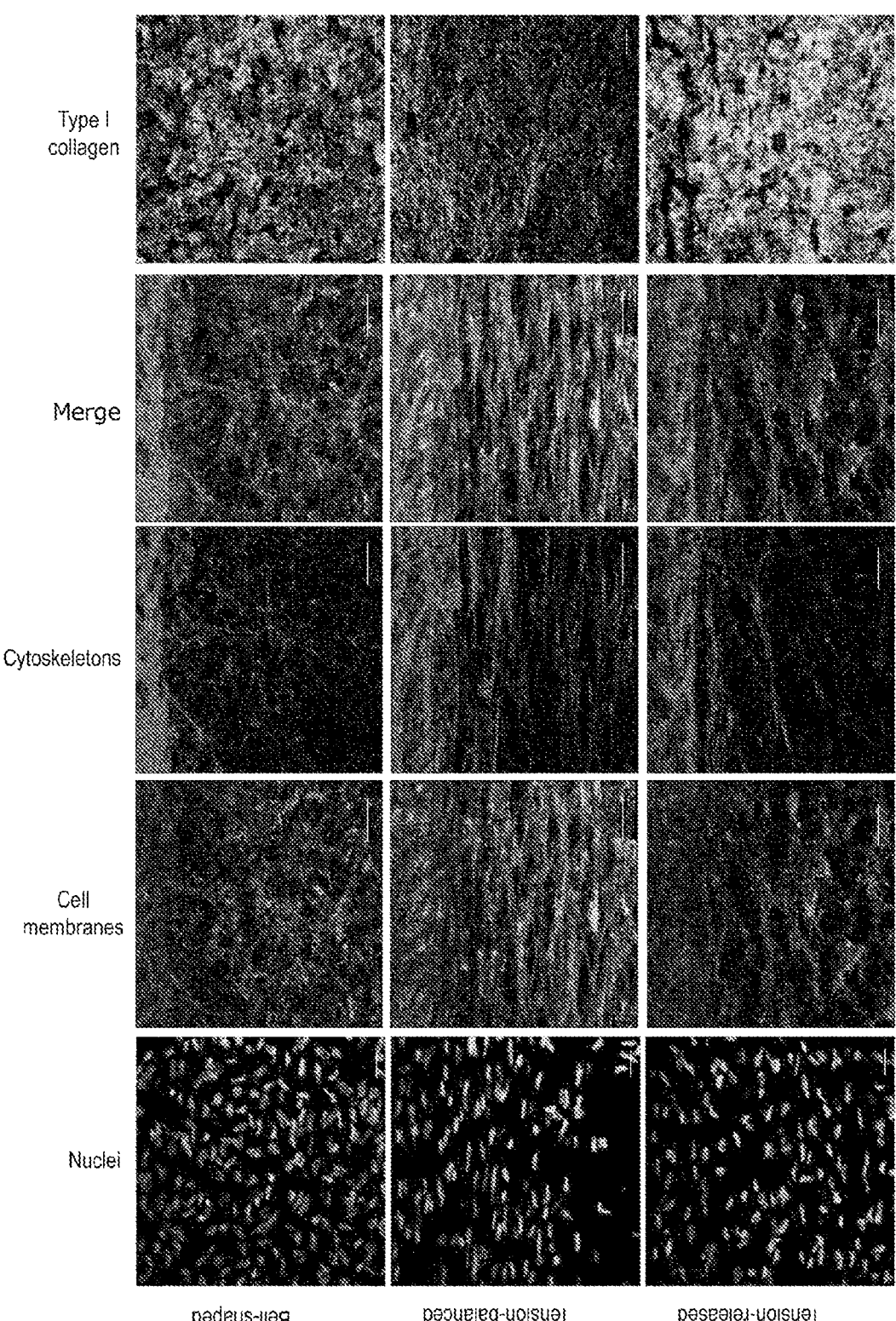
FIG. 9 is a series of images illustrating changes in morphology of dermis fibroblasts and collagen fibers by tension homeostatic stimulation.
Figure 10:
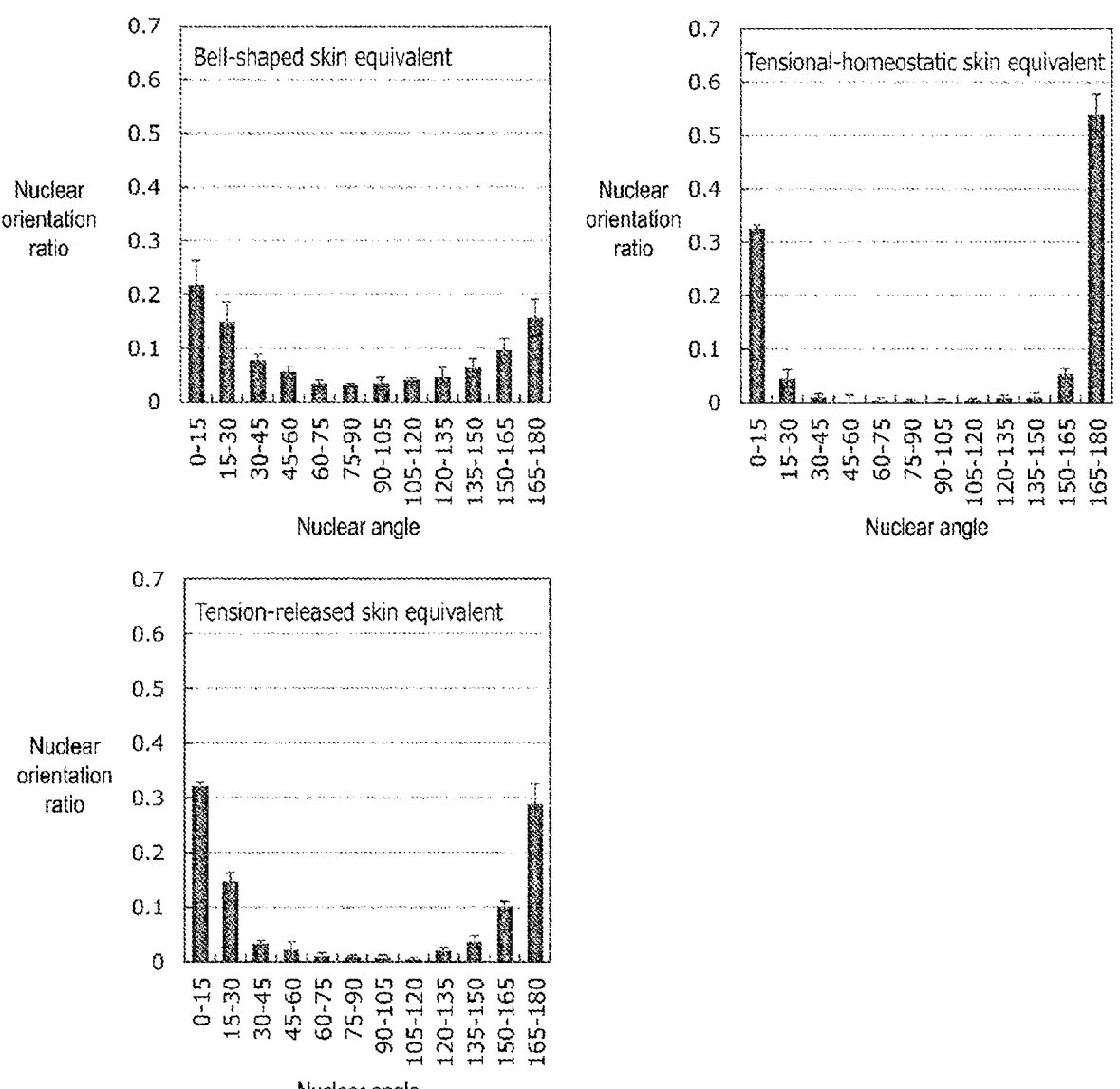
FIG. 10 is a series of graphs showing changes in nuclear orientations of dermis fibroblasts by tension homeostatic stimulation.
Figure 11:
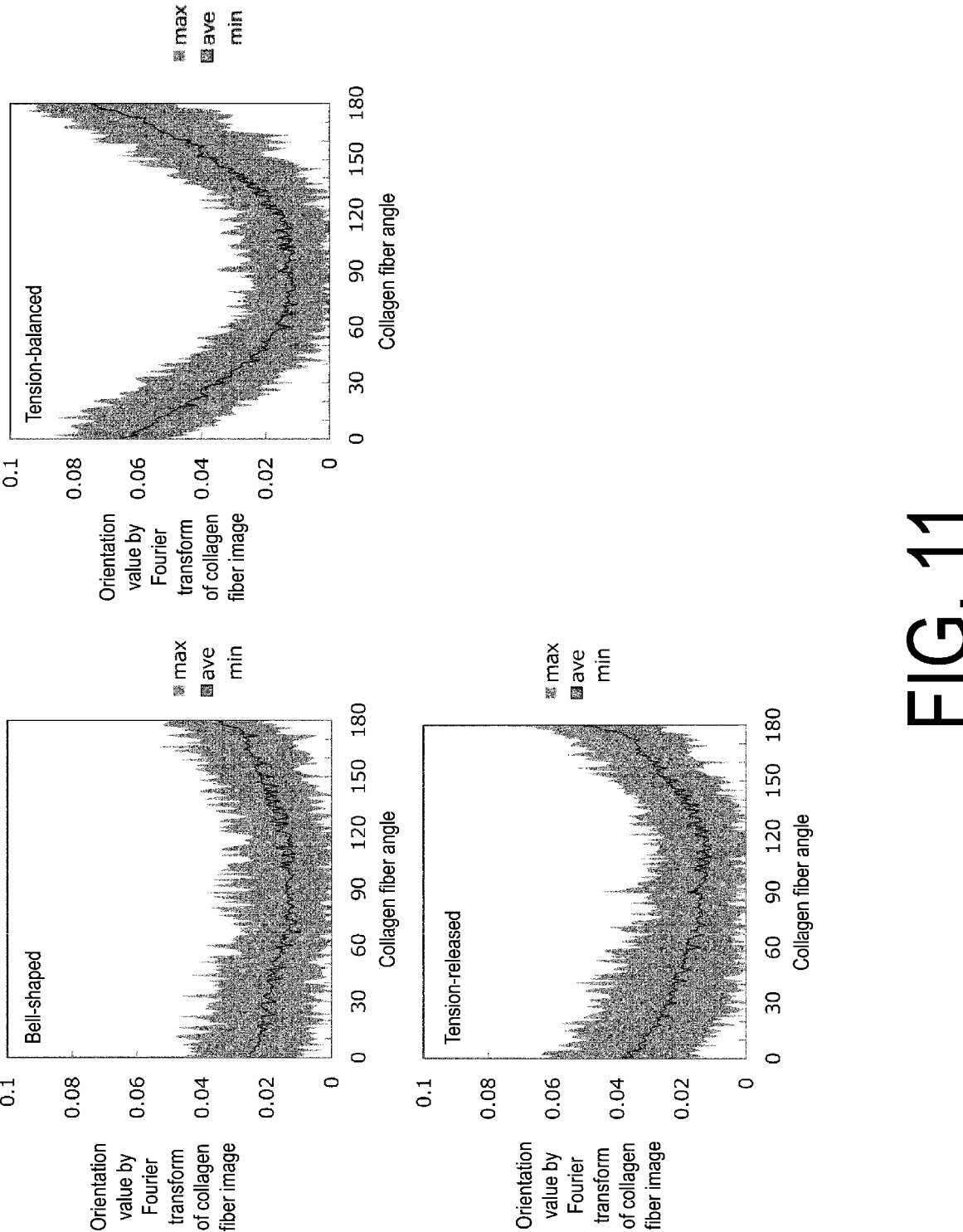
FIG. 11 is a series of graphs showing evaluation, obtained by two-dimensional Fourier transform, of orientations of collagen fibers of dermis fibroblasts by tension homeostatic stimulation.

The morphologies of nuclei, cell membranes, cytoskeletons, and collagen fibers of the fibroblasts in each skin equivalent model are shown in FIG. 9. Furthermore, the analysis results of the orientation of the nuclei are shown in FIG. 10. In the Tensional homeostatic skin model, the orientation of nuclei aligned in the same horizontal direction as the tensile direction was observed compared with the bell-shaped skin equivalent without tension. This directionality disappeared by the tension release and its structure changed to a structure similar to that in the bell-shaped skin equivalent. In addition, the analysis results of the orientation of the collagen fibers by two-dimensional fast Fourier transform are shown in FIG. 11. In the bell-shaped skin equivalent without tension, aggregates of collagen fibers without orientation were observed, whereas in the Tensional homeostatic skin model, in which tension homeostatic stimulation was applied, the orientation of collagen fibers aligned in the same horizontal direction as the tension direction was observed. This directionality disappeared by the tension release and its structure changed to a structure similar to that in the bell-shaped skin equivalent.

The results described above confirmed that, in the tensional homeostatic skin equivalent model, the improved ECM synthesis function, the improved type I collagen synthesis function, the epidermal keratinocyte ability proliferation promotion and the turnover promotion resulting therefrom, the proliferation promotion of epidermal keratinocytes, and the orientation of collagen fibers aligned in the same horizontal direction as the tension direction. In the tensional homeostatic skin equivalent model reflecting the actual good skin condition, the tensional homeostasis is considered to promote the expression of the mechanical stress signaling molecules (ITGA2, MRTFA, ACTA2 (αSMA)), and additionally, the tensional homeostasis is considered to maintain the improved ECM synthesis function, the improved type I collagen synthesis function, the epidermal keratinocyte ability proliferation promotion and the turnover promotion resulting therefrom, the proliferation promotion of epidermal keratinocytes, and the orientation of collagen fibers aligned in the same horizontal direction as the tension direction, which are observed in the normal skin tissue.

Example 3: Screening and Skin Functionality Evaluation of Mechanical Stress Signaling Activation Material For three skin equivalents of: a bell-shaped skin equivalent; a tensional homeostatic skin equivalent model; and a tension-released skin equivalent model, prepared in the same manner as in Example 1, after gas phase culture for 3 days, the medium was replaced with a medium for drug evaluation containing 1% fetal bovine serum, 1% penicillin/streptomycin, 5 µg/mL insulin (FUJIFILM Wako Pure Chemical Corporation), and 1 µM hydrocortisone (FUJIFILM Wako Pure Chemical Corporation), and preculture was performed for 48 hours. The medium was then replaced with a medium for drug evaluation containing 10 µM all-trans retinoic acid (ATRA), a mechanical stress activation material, and culture was performed for 6 to 48 hours.

The tissues were collected after completion of the culture. Total RNA was recovered from each tissue, and a real-time PCR was performed in the same manner as in Example 1. Genes analyzed for expression were MRTFA and ACTA2, which are mechanical stress signaling genes, and COL1A1 and HAS3, which are genes related to ECM synthesis function. The measured expression value of each gene was corrected by the ΔΔCT method by setting GAPDH as the endogenous gene expression control.

Furthermore, a portion of the collected tissue was immediately fixed in 4% paraformaldehyde phosphate buffer, a paraffin section was prepared by a common method, and immunohistochemical staining for type I collagen was performed by the following procedure.

Type I Collagen

Immunohistochemical staining was performed using a rabbit anti-human type I collagen antibody (Abcam. plc) and an Alexa Fluor 594-labeled anti-rabbit IgG antibody (Invitrogen). The nuclei of the stained tissue were stained using Hoechst 33342 (Thermo Fisher Scientific Inc.), and the nuclei (excitation wavelength: 350 nm, observation wavelength 470 nm) and a total level and localization of type I collagen expression (excitation wavelength 594 nm, observation wavelength 620 nm) were observed using a confocal microscope.

Figure 12:
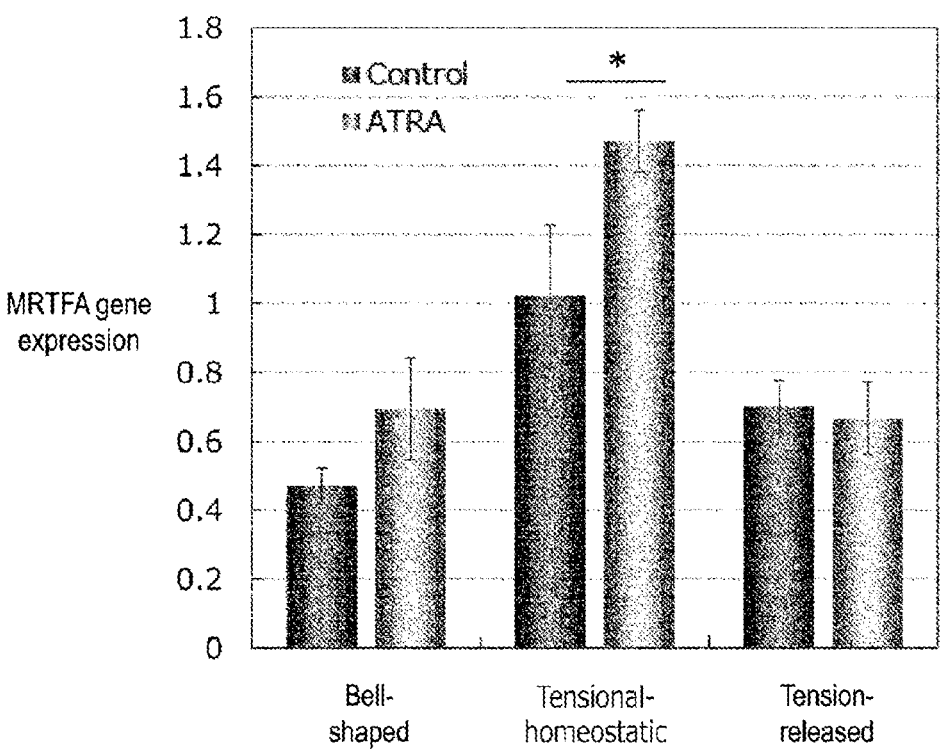
FIG. 12 is a graph showing MRTFA gene expression-inducing effect of ATRA administration on a tensional homeostatic skin equivalent model (TTEST *: P<0.01).

FIG. 12 is a plot of the MRTFA gene expression variation in each skin equivalent model in response to the ATRA administration. A significant increase in MRTFA gene expression by the ATRA administration was confirmed only in the tensional homeostatic skin equivalent model.

Figure 13:
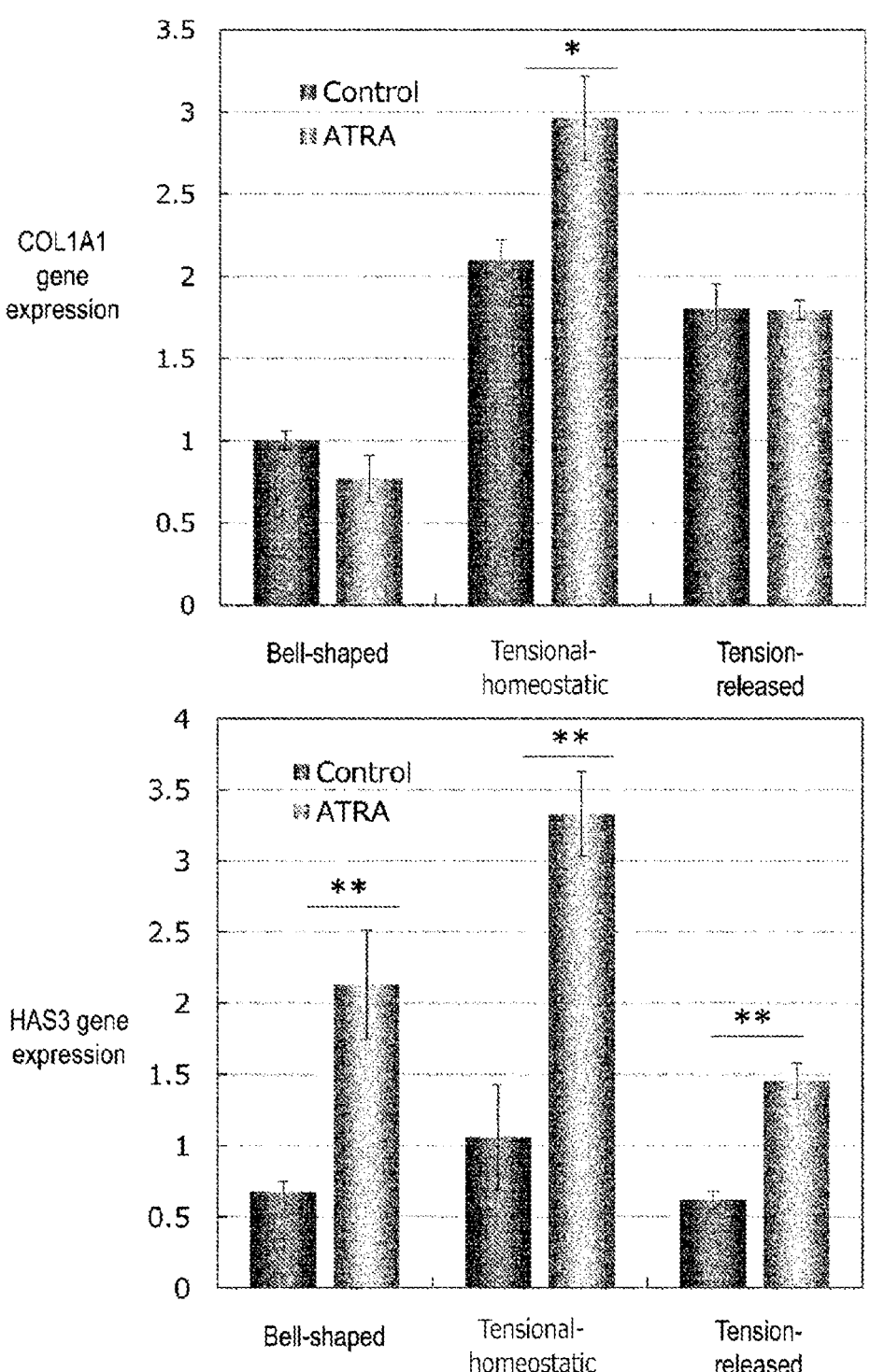
FIG. 13 is a series of graphs showing COL1A1 and HAS3 gene expression inducing effect of a mechanical stress signal promotion material (Tukey-Kramer Test *: P<0.01, **: P<0.001).

FIG. 13 is a series of plots of COL1A1 and HAS3 gene expression variations in each skin equivalent model in response to the ATRA administration. For the COL1A1 gene, significant promotion of gene expression by the ATRA administration was confirmed only in the Tensional homeostatic skin equivalent compared with the control group. For the HAS3 gene, significant promotion of gene expression by the ATRA administration was confirmed compared with all the control groups, but the ratio of the expression promotion showed the highest value in the Tensional homeostatic skin equivalent.

Figure 14:
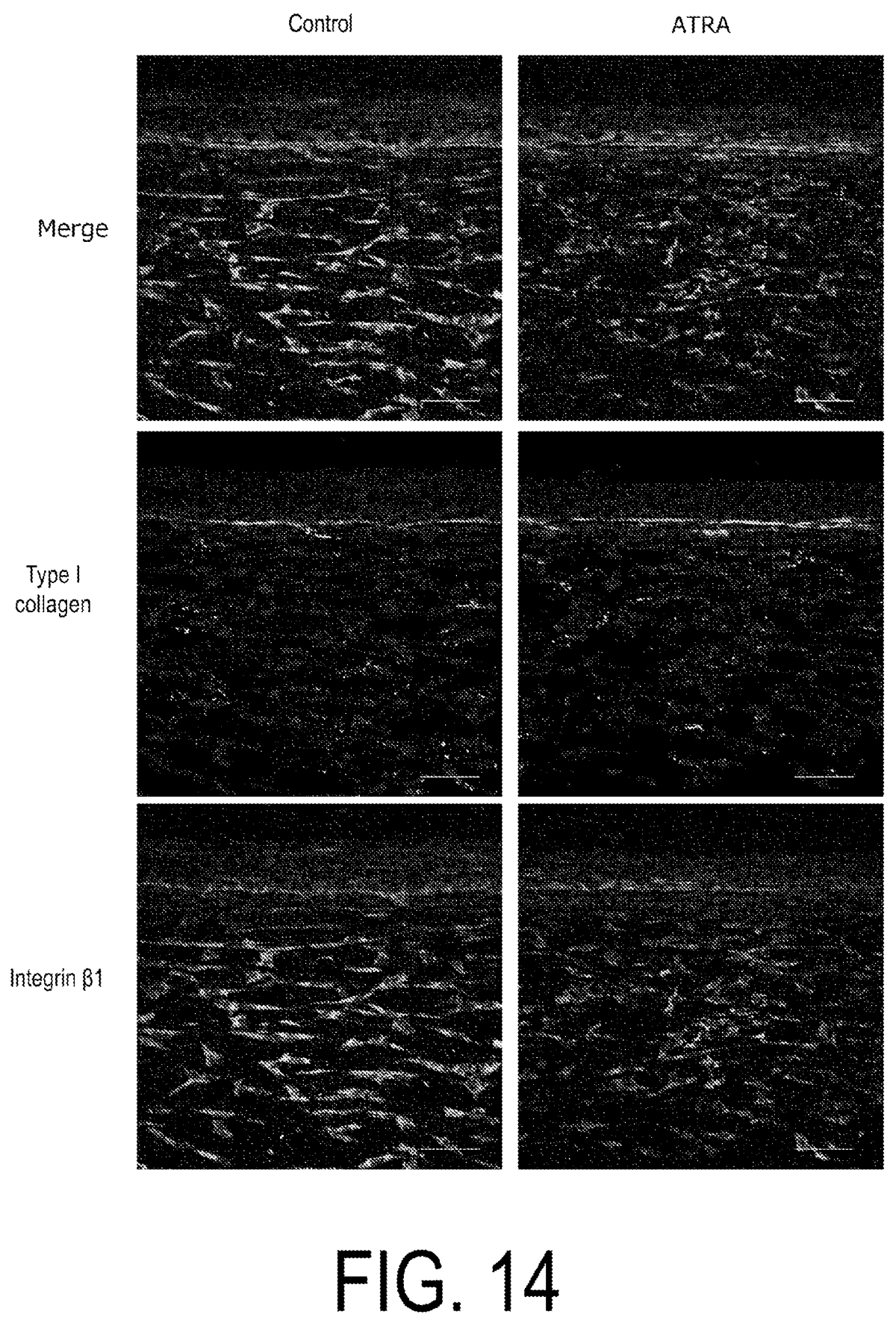

The immunohistochemical staining images of type I collagen in the Tensional homeostatic skin model are shown in FIG. 14. The expression of type I collagen increased in the ATRA administration group compared with the control group, confirming that the collagen fiber formation was promoted.

As described above, using the promotion of the expression of the mechanical stress signaling gene in skin cells as an index makes it possible to find a material (ATRA in the present example) that promotes collagen fiber formation under conditions close to the environment of a living body. In particular, the results confirmed that using the tensional homeostatic skin equivalent model reflecting the actual skin condition enables more efficient evaluation/screening.

Example 4: Evaluation of Skin Functionality by Mechanical Stress Signaling Inhibitory Material For three skin equivalents of: a bell-shaped skin equivalent; a tensional homeostatic skin equivalent model; and a tension-released skin equivalent model, prepared in the same manner as in Example 1, after gas phase culture for 3 days, the medium was replaced with a medium for drug evaluation containing 1% fetal bovine serum, 1% penicillin/streptomycin, 5 μg/mL insulin (FUJIFILM Wako Pure Chemical Corporation), and 1 μM hydrocortisone (FUJIFILM Wako Pure Chemical Corporation), and preculture was performed for 48 hours. The medium was then replaced with a medium for drug evaluation containing 10 nM Y-27632 (R&D Systems, Inc.), a mechanical stress inhibitory material, and culture was performed for 6 to 48 hours.

The tissues were collected after completion of the culture. Total RNA was recovered from each tissue, and a real-time PCR was performed in the same manner as in Example 1. The genes analyzed for expression were COL1A1, COL1A2, FBN1, ELN, and MMP1, which are genes related to ECM synthesis function. The measured expression value of each gene was corrected by the ΔΔCT method by setting GAPDH as the endogenous gene expression control.

Furthermore, a portion of the collected tissue was immediately fixed in 4% paraformaldehyde phosphate buffer, a paraffin section was prepared by a common method, and immunohistochemical staining for mechanical stress signaling molecules (ITGA2, MRTFA, and αSMA) and type I collagen was performed. The mechanical stress signaling molecules (ITGA2, MRTFA, and αSMA) were stained in the same manner as in Example 1, and type I collagen was stained by the following procedure. In addition, the actin cytoskeleton and cell membrane were observed by the following procedure.

Type I Collagen

Immunohistochemical staining was performed using a rabbit anti-human type I collagen antibody (Abcam. plc) and an Alexa Fluor 594-labeled anti-rabbit IgG antibody (Thermo Fisher Scientific Inc.). The nuclei of the stained tissue were stained using Hoechst 33342 (Thermo Fisher Scientific Inc.), and the nuclei (excitation wavelength: 350 nm, observation wavelength 470 nm) and a total level and localization of type I collagen expression (excitation wavelength 594 nm, observation wavelength 620 nm) were observed using a confocal microscope.

Actin Cytoskeleton and Cell Membrane

Fluorescent tissue staining was performed using Alexa 594-labeled phalloidin (Thermo Fisher Scientific Inc.) and Alexa 488-labelled WGA (Thermo Fisher Scientific Inc.). The nuclei of the stained tissue were stained using Hoechst 33342 (Thermo Fisher Scientific Inc.), and the nuclei (excitation wavelength: 350 nm, observation wavelength 470 nm), the actin cytoskeleton (excitation wavelength 594 nm, observation wavelength 620 nm), and cell membrane (excitation wavelength 488 nm, observation wavelength 535 nm) were observed using a confocal microscope.

Figure 15:
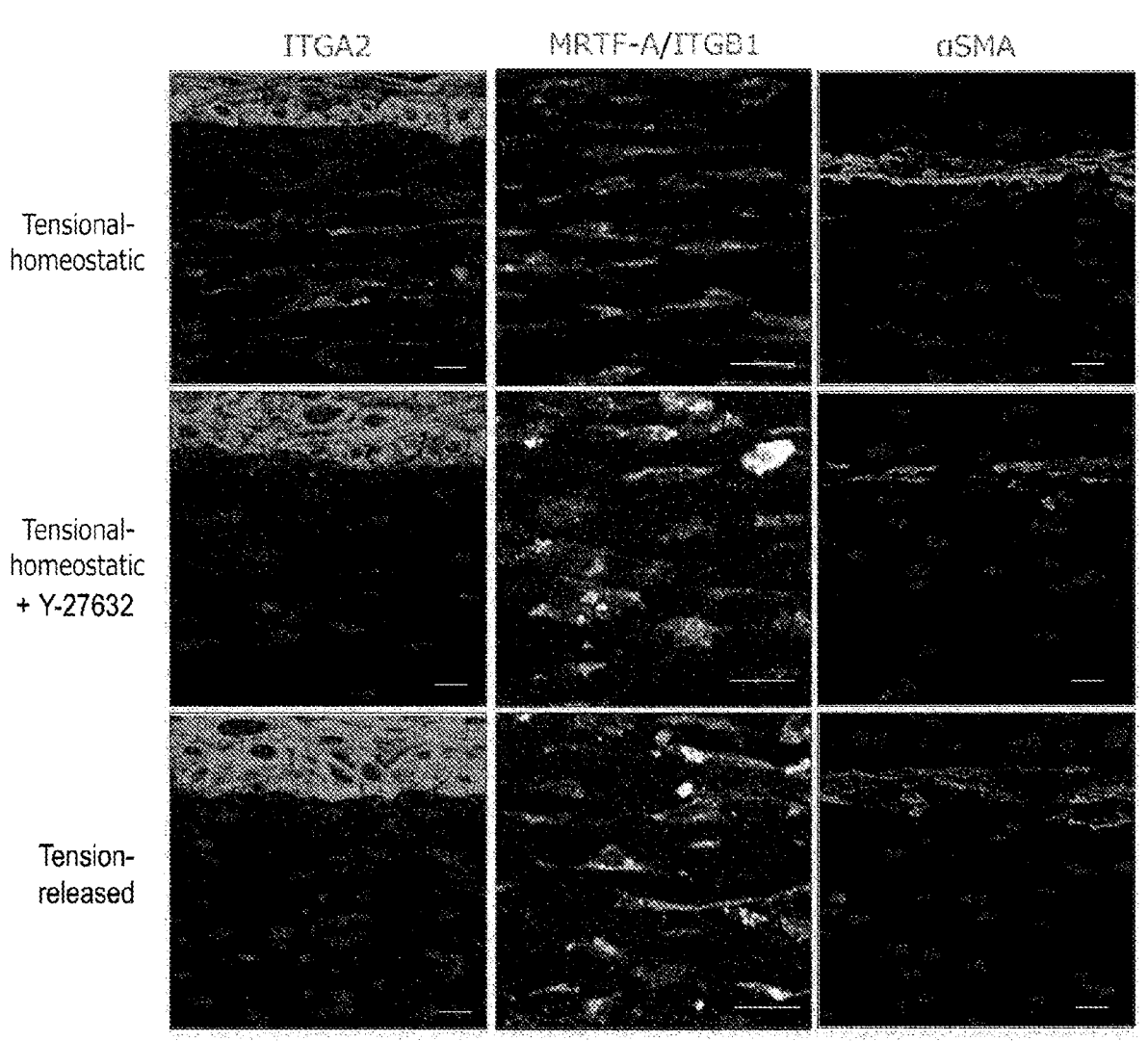
FIG. 15 is a series of images illustrating changes in expression and localization of mechanical stress signal molecules by Y27632.

FIG. 15 shows immunohistochemical staining images of the mechanical stress signal molecules in each skin equivalent model in response to the Y27632 administration. The images confirmed that the Y27632 administration to the tensional homeostatic model reduces the expression levels of ITGA2, MRTFA, and αSMA to the levels approximately equivalent to those in the tension-released model.

Figure 16:
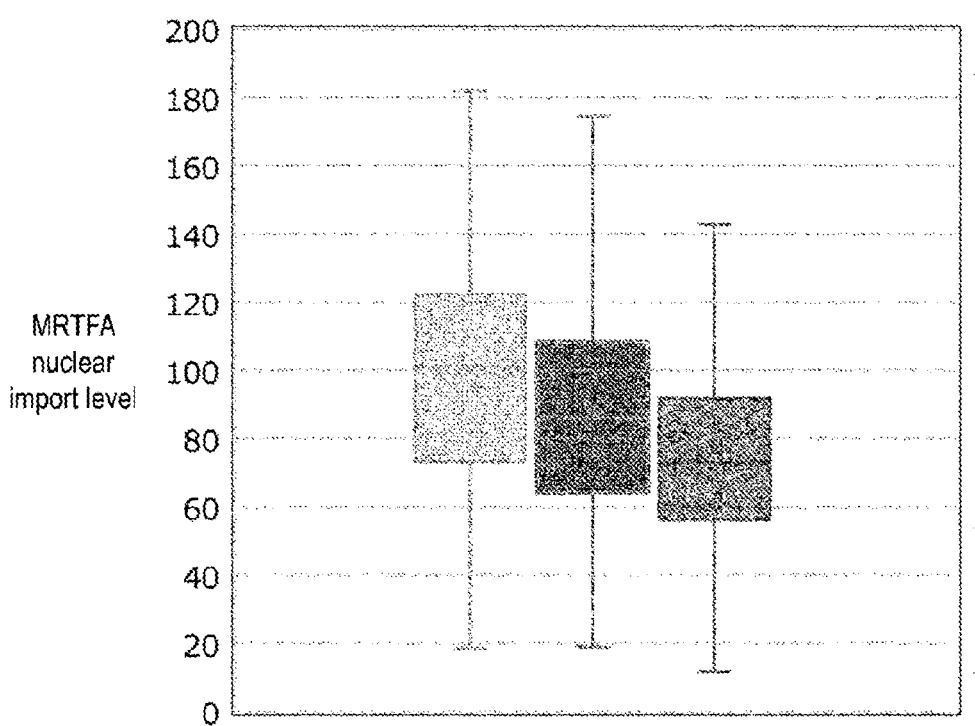
FIG. 16 is a graph showing changes in nuclear import rates of MRTFA by a mechanical stress signal inhibitory material.

FIG. 16 shows the results of the image analysis of the nuclear import rates of MRTFA. The Y27632 administration significantly reduced the nuclear import rates of MRTFA, confirming the inhibitory effect on the mechanical stress signal by Y27632.

Figure 17:
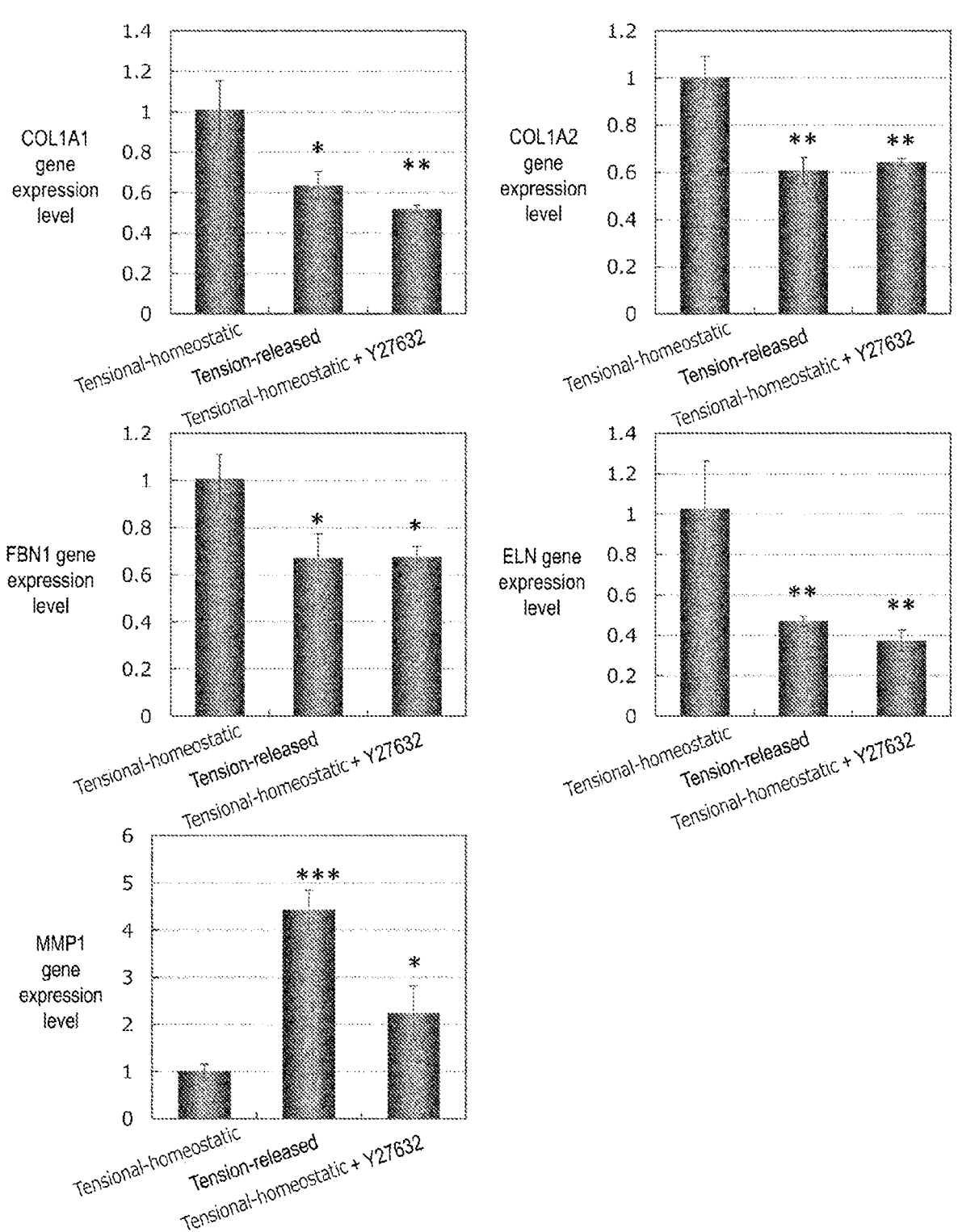
FIG. 17 is a series of graphs showing expression changes of ECM synthesis-related genes by a mechanical stress signal inhibitory material (Dunnett's Test *: P<0.05, : P<0.01, *: P<0.001).

FIG. 17 is a series of plots of the gene expression variations of COL1A1, COL1A2, FBN1, ELN, and MMP1 in each skin equivalent model in response to the ATRA administration. The Y27632 administration to the tensional homeostatic model significantly inhibited the gene expression of COL1A1, COL1A2, FBN1, and ELN involved in ECM synthesis to the equivalent level in the tension-released skin equivalent. Furthermore, the Y27632 administration significantly increased the gene expression of MMP1 involved in ECM degradation to the equivalent level in the tension-released skin equivalent.

Figure 18:
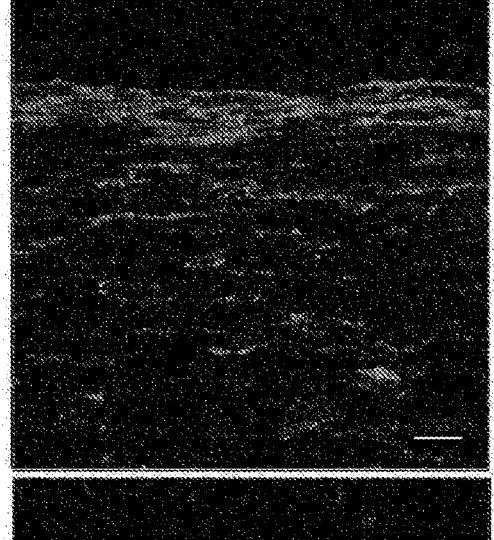
FIG. 18 is a series of images illustrating changes in type I collagen fiber formation by a mechanical stress signal inhibitory material.
Figure 18:
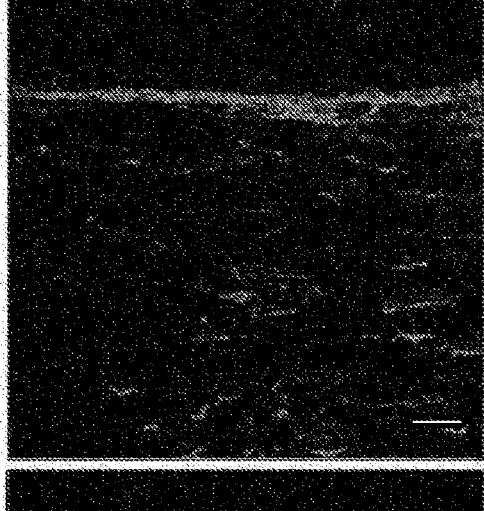
Figure 18:
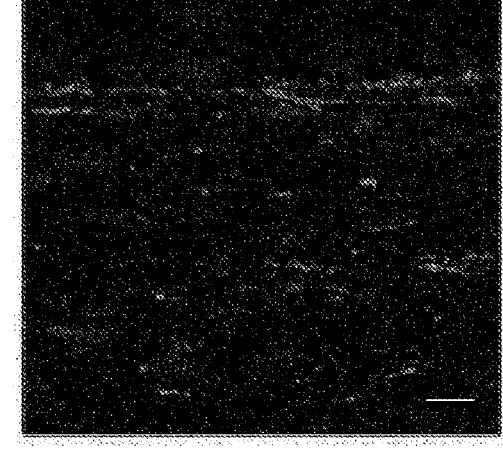

Immunohistochemical stain images of type I collagen are shown in FIG. 18. The Y27632 administration to the Tensional homeostatic skin equivalent reduced the expression level of type I collagen to the level approximately equivalent to that in the tension-released model, confirming inhibition of collagen fiber formation.

Figure 19:
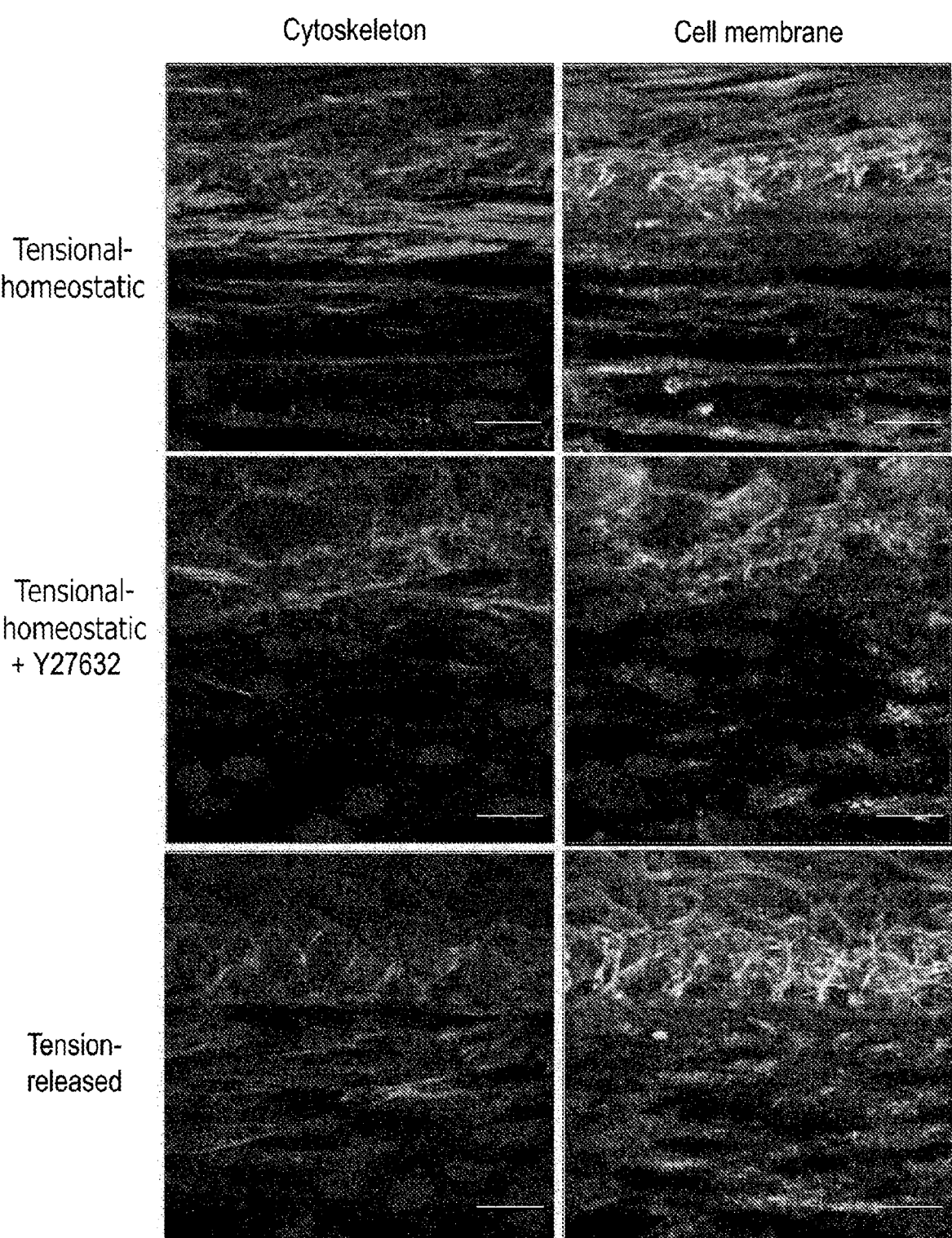
FIG. 19 is a series of images illustrating changes in tissue morphology by a mechanical stress signal inhibitory material.

Fluorescent staining images of the cytoskeleton and cell membrane are shown in FIG. 19. The Y27632 administration to the Tensional homeostatic skin equivalent reduced the orientations of the cytoskeletons, cell membranes, and nuclei in the tension direction to the level approximately equivalent to that in the tension-released model, confirming the disturbance of the orientation of the tissue.

As described above, using the inhibition of the expression of the mechanical stress signaling gene in skin cells as an index makes it possible to find a material (Y27632 in the present example) that acts toward the inhibition of collagen fiber formation, promotion of ECM degradation, and decrease in the orientation of the tissue. In particular, the results confirmed that using the tensional homeostatic skin equivalent model reflecting the actual skin condition enables more efficient evaluation/screening.

INDUSTRIAL APPLICABILITY

The method for evaluating and/or screening a control agent for tissue morphology and/or tissue function according to an embodiment of the present invention can identify a healthcare material or a pharmaceutical material that can transmit, to cells constituting tissues, a signal equivalent to a signal produced by mechanical stress, which a living body experiences in the normal state. A material to be found by the method according to an embodiment of the present invention can appropriately control the tissue morphology or tissue function of a living body and thus can be expected to be effective for symptoms caused by reduced mechanical stress. For example, the material is useful for treating deterioration in aesthetic appearance due to aging, such as wrinkles, sagging, blotches, reduced transparency, and enlarged pores in the skin; skin fibrosis, such as a scar, striae gravidarum, and keloid; and epithelial cell carcinoma.

The invention claimed is:

1. A method for evaluating and/or screening a control agent for skin morphology and/or skin function, the method comprising:
   applying a test substance to a continuous tension-homeostatic skin model comprising artificial dermis comprising normal human fibroblasts dispersed in a gel and capable of expressing a mechanical stress signaling molecule to identify a candidate substance; and
   evaluating expression, activity, or intracellular localization of the mechanical stress signaling molecule in the tension-homeostatic skin model, wherein the mechanical stress signaling molecule is at least one selected from the group consisting of ITGA2 (integrin alpha 2), MRTFA (myocardin-related transcription factor A), and ACTA2 (actin alpha 2).

2. The method according to claim 1, wherein, in the evaluating step, expression, activity, or intracellular localization of the mechanical stress signaling molecule is compared with a control.

3. The method according to claim 2, wherein the control is said tension-homeostatic skin model but with no test substance applied or only a solvent of the test substance applied.

4. The method according to claim 1, wherein the continuous tension-homeostatic skin model comprises a tension-related artificial dermis comprising normal human dermis fibroblasts and normal human epidermal keratinocytes.

5. The method according to claim 1, wherein said artificial dermis is prepared by dispersing and seeding normal human dermis fibroblasts in a gel, solidifying said gel, fixing the solidified gel in a culture vessel to apply continuous tension, and further seeding normal epidermal keratinocytes on said solidified gel.

6. The method according to claim 1, which further comprises subjecting said candidate substance identified by said evaluating step to further screening to confirm whether said candidate substance enhances, reduces, or otherwise alters the expression level, activity, or localization of said mechanical stress signaling molecule.

7. A method for evaluating and/or screening a control agent for skin morphology and/or skin function, the method comprising:
   applying a test substance to a tissue or cells taken from a mammal selected from skin tissue, epidermal tissue, dermis tissue, epidermal cells, or dermis cells, a culture of said tissue or cells, and a continuous tension homeostatic skin model composed of any of these capable of expressing a mechanical stress signaling molecule to identify a candidate substance; and
   evaluating expression, activity, or intracellular localization of the mechanical stress signaling molecule in the tension-homeostatic skin model,
   wherein the mechanical stress signaling molecule is at least one selected from the group consisting of ITGA2 (integrin alpha 2), MRTFA (myocardin-related transcription factor A), and ACTA2 (actin alpha 2).

8. The method according to claim 7, wherein the test substance is applied to epidermal keratinocytes.

9. The method according to claim 7, wherein the test substance is applied to dermal fibroblasts.

10. The method according to claim 7, wherein the test substance is applied to said established cell line of said tissue or cells.

11. The method according to claim 7, wherein, in the evaluating step, expression, activity, or intracellular localization of the mechanical stress signaling molecule is compared with a control group.

12. The method according to claim 11, wherein the control group include those having the same tissue or cell as that of the test group but with no test substance applied or only a solvent of the test substance applied.

13. The method according to claim 7, which further comprises subjecting said candidate substance identified by said evaluating step to further screening to confirm whether said candidate substance enhances, reduces, or otherwise alters the expression level, activity, or localization of said mechanical stress signaling molecule.

* * * * *